US006310085B1

(12) United States Patent
Willis

(10) Patent No.: US 6,310,085 B1
(45) Date of Patent: Oct. 30, 2001

(54) METHOD FOR THE TREATMENT OF NEUROLOGICAL OR NEUROPSYCHIATRIC DISORDERS

(75) Inventor: Gregory Lynn Willis, Woodend (AU)

(73) Assignee: Clarencew Pty Ltd., East Melbourne (AU)

(*) Notice: Subject to any disclaimer, the term of this patent is extended or adjusted under 35 U.S.C. 154(b) by 0 days.

(21) Appl. No.: 09/285,859

(22) Filed: Apr. 2, 1999

Related U.S. Application Data

(63) Continuation-in-part of application No. PCT/AU97/00661, filed on Oct. 3, 1997.

(51) Int. Cl.[7] ................................................ A61K 31/405
(52) U.S. Cl. ............................................................ 514/415
(58) Field of Search ............................................. 514/415

(56) References Cited

U.S. PATENT DOCUMENTS

| | | |
|---|---|---|
| 4,880,826 | 11/1989 | Zisapel et al. . |
| 5,046,494 | 9/1991 | Searfoss et al. . |
| 5,071,875 * | 12/1991 | Horn et al. ........................... 514/613 |
| 5,093,352 | 3/1992 | Dubocovich . |
| 5,137,018 | 8/1992 | Chuprikov et al. . |
| 5,283,343 | 2/1994 | Dubocovich et al. . |
| 5,552,418 * | 9/1996 | Depreux et al. ..................... 514/348 |
| 5,616,614 | 4/1997 | Yous et al. . |

FOREIGN PATENT DOCUMENTS

| | | |
|---|---|---|
| 0 146 113 | 6/1985 | (EP) . |
| WO 95/29173 | 11/1995 | (WO) . |

OTHER PUBLICATIONS

The Merk Manual of Diagnosis and Therapy, 16th Edition, published 1992 By Merk Research Laboratories pp. 1499, 1634, and 1640.

Alder, et al. (1991) vol. 27, No. 2, pp. 107–111, "Studies on the Time Course and efficacy of beta–blockers in neuroleptic–induced akathisia and the akathisia of idopathic Parkinson's disease" Pychopharmacology Bulletin.

A.R. Artmenko, et al., Medline Abstract accession No: VI : 96438011, "The Phototherapy of Parkonsonian Therapy" Arch Neurol. vol. 44, Jan. 1996.

Koller, et al. (1987) "Aduvant Therapy of Parkinsonian Therapy" Arch Neurol. vol. 44, pp. 921–923.

Martindale, The Extra Pharmacopoeia 28th Edition, published 1982 by The Pharmaceutical Press, pp. 1337, 1332, and 1334.

Miles, et al. (1988) "Melatonin and Psychiatry"Biol. Psychiatry, vol. 23, pp. 405–425.

Sandyk, R. (1993), Intern. J. Neuroscience, vol. 68, pp. 85–91.

Sandyk, R. (1992), Intern. J. Neuroscience, vol. 66, pp. 1–15.

Sherer, et al. (1985), 58 (3) : 277–282, "Effects of melatonin on performance testing the patients with seasonal affective disorder", Neurosci. Lett.

Talavera– Garcia, Barajas, et al. Medline Abstract, accession No: UI:85136415 "Atenolol in the control of Parkinsonian Tremor", (1984).

Wilbur, et al. (1988) "Noradrenergic effects in tardive dyskinesia, akathisia and pseudoparkinsonism via the limbic system and basal ganglia" Prog. Neuro–Psychoparmacol and Biol. Psychiat., vol. 12, pp. 849–864.

* cited by examiner

*Primary Examiner*—William R. A. Jarvis
(74) *Attorney, Agent, or Firm*—Rothwell, Figg, Ernst & Manbeck

(57) ABSTRACT

This invention relates to a method for the treatment and/or prophylaxis of a neurological or neuropsychiatric disorder associated with altered dopamine function which comprises subjecting a patient in need thereof to therapy which blocks and/or inhibits melatonin, precursors thereof and/or metabolic products thereof.

20 Claims, 20 Drawing Sheets

METHOD FOR THE TREATMENT OF NEUROLOGICAL OR NEUROPSYCHIATRIC DISORDERS

CROSS REFERENCE TO RELATED APPLICATIONS

This is a Continuation-in-part application of International Patent Application No. PCT/AU97/00661, filed on Oct. 3, 1997.

The present invention relates generally to a method for the treatment and/or prophylaxis of neurological or neuropsychiatric disorders, in particular neurological or neuropsychiatric disorders associated with altered dopamine function.

The pineal body, situated in the epithalamus at the centre of the brain, synthesises and releases melatonin into the general circulation only during nocturnal darkness, irrespective of whether a species is nocturnal or diurnal in its behavioural activity pattern. In mammals, the rhythm of pineal nocturnal melatonin secretion is generated by a biological clock located at the suprachiasmatic nuclei (hereinafter referred to as "SCN") of the anterior hypothalamus. After following a circuitous route through the brain, afferent pathways of the conarian nerves originating from the superior cervical ganglia end in sympathetic innervation on pinealocytes. In humans, the only natural phenomenon presently known to inhibit melatonin release is bright light. Melatonin release appears to be robust and resistant to change by a variety of potent stimuli. The stability of the melatonin rhythm makes melatonin an ideal candidate as a biological timing hormone, a role which is indisputable for rhythms in photo-sensitive seasonal breeding mammals and has been postulated for daily rhythms in non-seasonal breeders.

Daily injections of melatonin entrains free-running locomotor activity rhythms of rats housed in constant darkness or constant light, influences the speed and direction of re-entrainment to phase shifts in the light-dark cycle and reorganises and recyncronises the disrupted components of the circadian system. These entrainment effects are dependant upon on the integrity of the SCN biological clock which is a structure containing high affinity melatonin receptors. In addition to these effects of exogenous melatonin on the pattern of locomotor activity, there are early unconfirmed reports that melatonin injections, pineal extracts and pinealectomy affect the amount of locomotor activity. Although such reports are unconfirmed, they raise the possibility of a more direct action on the locomotor system per se, rather than the indirect effect via the SCN. This would be consistent with the more recent reports involving animal models of movement disorders such as those where a decrease in spontaneous motor activity in mice is found with both peripheral (1) and intranigral (2) injection of melatonin as well as melatonin blockade of L-Dopa induced movement (3) and melatonin modulation of apomorphine induced rotational behaviour (4). Against this background, early reports of amelioration of Parkinson's disease by administration of high doses of melatonin appears possible (5). In view of the role of dopamine in Parkinson's disease and other motor disorders, a common link between each of these disorders is a change in dopamine function.

Clinical studies examining the role of melatonin in neuropsychiatric disorders have been limited in number and are inconsistent in their reported findings and hypothesised role of this hormone. It was suggested by MacIsac (6) that melatonin was involved in the precipitation of many symptoms of schizophrenia. This hypothesis was in accordance with the conjecture that the pineal was overactive in this disorder (7). However, other clinical studies have revealed that nocturnal melatonin secretion is reduced in chronic schizophrenia (8) and some have paralleled the negative symptoms of this disease with those of Parkinson's disease (9) indicating that melatonin provides a protective effect against the development of the negative symptoms of schizophrenia and Parkinson's disease from the time puberty commences (10). This hypothesis is supported further by findings implicating pineal deficiency in schizophrenia (11). Additional confusion has arisen as to the role of melatonin in the aetiology of schizophrenia as a result of experiments where bovine pineal extract was administered to patient's suffering from this disorder causing a reversal of biochemical abnormalities and clinical improvement (12). However, later repetition of these studies did not yield results which were clinically meaningful ( 13).

The psychopharmacology of psychosis does not aid in clarifying the role of melatonin in these disorders. The administration of β-adrenergic blockers, sometimes used as an anti-psychotic medication, reduces plasma levels of melatonin (14) while chlorpromazine, increases melatonin (15). However, since other anti-psychotics do not elevate melatonin concentrations (16), the hypothesis that melatonergic function is altered in schizophrenics and that effective medications might work via the melatonergic system (17) have gained little support.

The picture becomes further obscured when the results from studies whereby melatonin was administered for prolonged periods to patients suffering from Parkinson's disease are considered. Daily doses of 1000–1200 mg of melatonin per day have been reported to produce a 20–36% amelioration of the clinical features (18) and a significant reduction in tremor (19). However, replication of that work, with similar doses over the same time period did not improve the cardinal features of Parkinson's disease (20). It has also been claimed that pineal secretory activity was diminished in this disease (21) and that melatonin itself could be useful in alleviating the symptoms of Parkinsonism (22). Consideration of the findings from other research (23) where the relationship between agonist therapy and melatonergic activity was examined, arrived at the conclusion that Parkinson's disease did not result from pathology of the melatonergic system. Later research (24) revealed no major changes in melatonin rhythm or changes in plasma melatonin concentrations after dopamine agonist therapy. Bearing in mind the antioxidant properties of melatonin (25) and the current trend in attempting to halt the progressive degeneration of Parkinson's disease by implementing antioxidants (26), this deflates any attempt to explain Parkinson's disease on the basis of pathological function of the pineal.

The role of melatonin in clinical disorders of appetite is believed to be of minimal significance. While plasma melatonin concentrations are significantly reduced in the sub-population of anorexics which exhibit depression(27), this has been attributed to the depression rather than a pathological feature of anorexia nervosa or anorexia bulimia(28). Changes in the circadian periodicity of melatonin secretion has been detected in about one third of patients suffering from anorexia nervosa or anorexia bulimia(29). However, the increase in melatonin was suggested as being due to chronic malnutrition or sustained physical exercise and lends little support to the interpretation that pathophysiology of the melatonergic system plays a significant role in such disorders.

We have now discovered the specific mechanism by which melatonin may be exacerbating motor disability and a number of related disorders of motor function. This finding provides a rational basis upon which neurological or neuropsychiatric disorders can be treated and is designed to block and/or inhibit the activity of melatonin.

According to one aspect of the present invention there is provided a method for the treatment and/or prophylaxis of a neurological or neuropsychiatric disorder associated with altered dopamine function which comprises subjecting a patient in need thereof to therapy which blocks and/or inhibits melatonin, precursors thereof and/or metabolic products thereof.

The present invention also provides the use of therapy which blocks and/or inhibits melatonin, precursors thereof and/or metabolic products thereof in the treatment and/or prophylaxis of a neurological or neuropsychiatric disorder associated with altered dopamine function.

Throughout this specification, unless the context requires otherwise, the word "comprise", or variations such as "comprises" or "comprising", will be understood to imply the inclusion of a stated integer or group of integers but not the exclusion of any other integer or group of integers.

The neurological or neuropsychiatric disorders associated with altered dopamine function may include movement disorders, such as, Huntington's chorea, periodic limb movement syndrome, restless leg syndrome (akathesia), Tourrette's syndrome, Sundowner's syndrome, schizophrenia, Pick's disease, Punch drunk syndrome, progressive subnuclear palsy, Korsakow-s (Korsakoff's) syndrome, Multiple Sclerosis or Parkinson's disease; medication-induced movement disorders, such as, neuroleptic-induced Parkinsonism, malignant syndrome, acute dystonia, stroke, trans-ischaemic attack, tardive dyskiesia or multiple systems atrophy (Parkinson's plus); eating disorders, such as, anorexia cachexia or anorexia nervosa; and cognitive disorders, such as, Alzheimer's disease or dementia, for example, pseudo dementia, hydrocephalic dementia, subcortical dementia or dementia due to Huntington's chorea or Parkinson's disease; psychiatric disorders characterised by anxiety such as panic disorder, agoraphobia, obsessive-compulsive disorder, post traumatic stress disorder, acute stress disorder, generalised anxiety disorder and anxiety disorders due to other medical disorders, such as, depression.

Preferably the method according to the present invention is used to treat Parkinson's disease, schizophrenia, restless leg syndrome, tardive diskinesia, generalised anxiety disorders or to treat one or more, preferably two or more, of the Parkinsorian symptoms associated with movement disorders. The recognised symptoms or characteristics of Parkinson's disease are bradykinesia (slowness of movement), rigidity and tremor.

As used herein the terms "Parkinson's disease", "Parkinson's" and "Parkinsonism" are to be understood to include the various forms of the condition including idiosyncratic Parkinson's disease, post-encephaletic Parkinson's disease, drug induced Parkinson's disease, such as neuroleptic induced Parkinsorism, and post-ischemic Parkinsonism.

When dopamine containing neurones of the brain undergo degeneration there are two immediate consequences. One is the interference of normal synaptic transmission which is ultimately characterised by a depletion of functional dopamine (accompanied by a change in receptor number, affinity, etc.) resulting in decreased neurotransmission thereby affecting normal synaptic relations with adjacent neurones. Various neurological and neuropsychiatric disorders such as Parkinsonism are currently viewed as being due to depletion of brain dopamine. However, in the present invention increased brain dopamine is used as the biological marker to point to the mechanism underlying the alleviation of motor impairment, and associated states of anxiety and depression. Therefore from this perspective the altered dopamine function associated with neurological or neuropsychiatric disorders is generally characterised by a change in dopamine function.

The therapy may involve subjecting the patient to an external therapy which blocks and/or inhibits melatonin, precursors thereof and/or metabolic products thereof, for example, light therapy, and/or the administration of an agent which blocks and/or inhibits melatonin, precursors thereof and/or metabolic products thereof, such as, a melatonin antagonist, β-adrenergic antagonists, for example, propranolol or atenolol, calcium channel blockers or melanocyte stimulating hormone (MSH) and/or surgical ablation or destruction of the pineal gland (pinealectomy). The melatonin antagonist may include a melatonin analogue or metabolite or any other indolamine, neurotransmitter, neuromodulator, neurohormone or neuropeptide which has an affinity for melatonin receptors and thereby interferes with normal melatonergic function. The agent may be administered alone or in conjunction with light therapy or medicaments used in the treatment of neurological or neuropsychiatric disorders, such as, for example, domperidone, haloperidol, pimnozide, clozapine, sulpiride, etaclopromide, spiroperidol or an inhibitor of dopamine neurotransmission.

A number of melatonin antagonists have been reported in the literature. For example U.S. Pat. No. 4,880,826 and U.S. Pat. No. 5,616,614 report two different chemical classes of melatonin antagonists, the compounds of formula (1) and formula (2) respectively.

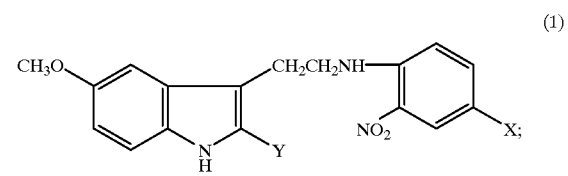

(1)

In formula (1) X is —$NO_2$, —$N_3$, Y is—H, I,

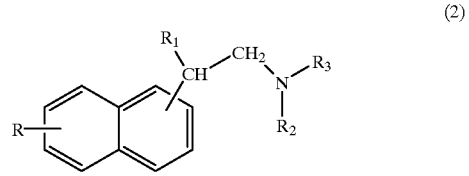

(2)

In formula (2)

R represents a hydrogen atom or a group —O—$R_4$ in which $R_4$ denotes a hydrogen atom or a substituted or unsubstituted group chosen from alkyl, cycloalkyl, cycloalkylaikyl, phenyl, phenylalkyl and diphenylaiky, $R_1$ represents a hydrogen atom or a group —CO—O—$R_5$ in which $R_5$ denotes a hydrogen atom or a substituted or unsubstituted alkyl group, $R_2$ represents a hydrogen atom or a group —$R^1_2$ with $R^1_2$ representing an alkyl or substituted alkyl radical, $R_3$ represents

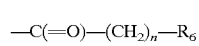

—C(=O)—$(CH_2)_n$—$R_6$ in which n represents O or an integer from 1 to 3 and $R_6$ represents a hydrogen atom or an alkyl, substituted alkyl alkene, substituted alkene, cycloalkyl or substituted cycloalkyl group, or a substituted or unsubstituted heterocyclic group chosen from pyrrolidine, piperidine, piperazine, homopiperdine, homopiperazine, morpholine and thiomorpholine;

in which X represents an oxygen or sulfur atom, n' represents O or an integer from 1 to 3 and $R_7$ represents an alkyl, substituted alky, cycloalkyl, substituted cycloalkyl, phenyl or substituted phenyl group, on the understanding that if:

R represents an alkoxy group,

R represents a hydrogen atom and $R_3$ represents a group —CO—$R_8$ in which $R_{11}$ represents a hydrogen atom, a methyl group or a methyl or propyl group substituted with a halogen, or if $R_3$ represents a group —C(=X)—NH—$(CH_2)_{11}$—$R_7$ in which X, n' and $R_7$ are as defined above, then $R_1$ cannot be a hydrogen atom, their optical isomers and their addition salts with a pharmaceutically acceptable base, on the understanding that, except where otherwise specified, the term "substituted" means that the groups to which it relates may be substituted with one or more radicals chosen from halogen, $(C_1-C_4)$alkyl, $(C_1-C_4)$ alkoxy, phenyl and phenylalkyl, it being possible for the phenyl rings themselves to be substituted with one or more halogen, $(C_1-C_4)$ alkyl, $(C_1-C_4)$ alkoxy, hydroxyl or trifluoromethyl radicals, the term "alkyl" denotes a group containing from 1 to 6 carbon atoms in an unbranched or branched chain, the term "alkene" denotes a group containing from 2 to 6 carbon atoms in an unbranched or branched chain, the term "cycloalkyl" denotes a saturated or unsaturated, mono- or bicyclic group containing from 3 to 10 carbon atoms.

Among pharmaceutically acceptable bases which can be used to form an addition salt with the compounds of the invention, there may be mentioned, as examples and without implied limitation, sodium hydroxide, potassium hydroxide, calcium hydroxide or aluminum hydroxide, alkali metal or alkaline earth metal carbonates and organic bases such as triethylamine, benzylamine, diethanolamine, tert-butylamine, dicyclohexylamine and arginine.

The compounds of formula (1) and formula (2) are examples of agents which block and/or inhibit melatonin and are suitable agents for the purposes of the present invention. Other known or novel melatonin antagonists, whether they are known or novel, are expected also to be of use in the present invention, for example: compounds described in U.S. Pat. No. 5,283,343 which includes the compound known as luzindole, and compounds described in U.S. Pat. No. 5,093,352.

The compound of formula (1) where X=$NO_2$ and Y=H (known as ML-23) is a particularly preferred compound. The compound of formula (2) where R=H, $R_1$=H, $R_2$ =H, $R_3$=—C(=O)—$(CH_2)_n$—$R_6$ where n=0 and $R_6$ is a cyclobutyl group is known as S20928.

The therapy may also be performed in conjunction with ablation or destruction of areas of increased dopamine function in the brain, and/or with a drug therapy which alters doparmine function, such as the administration of a dopamine receptor blocker (antagonist), especially those neuroleptics described as atypical, such as clozapine and/or with a drug therapy with a β-adrenergic receptor antagonist, such as atenolol.

The typical levels at which melatonin may be blocked and/or inhibited:
  (i) the level of the signal from the brain to the pineal where release takes place;
  (ii) the level where synthesis takes place at the pinealocyte; and
  (iii) the level of the occupancy of receptors.

Thus, the therapy may block and/or inhibit not only melatonin itself, but precursors used in the production of melatonin, such as, for example, tryptophan, 5-hydroxytiyptophan, serotonin or N-acetylserotonin or metabolic products resulting from the breakdown of melatonin including enzymes or other catalysts, such as, for example, tryptophan hydroxylase, aromatic amino acid decarboxylase, N-acetyltransferase and hydroxyindole-O-methyltransferase. An example of products resulting from the breakdown of melatonin is 6-hydroxymelatonin sulphate.

In yet another aspect of the present invention there is provided a method for the treatment and/or prophylaxis of a neurological or neuropsychiatric disorder associated with altered dopamine function which comprises administering an effective amount of an agent which blocks and/or inhibits melatonin, precursors thereof and/or metabolic products thereof and a drug which alters dopamine function and optionally light therapy to a patient in need thereof.

According to another aspect of the present invention there is provided a method for the treatment and/or prophylaxis of a neurological or neuropsychiatric disorder associated with altered dopamine function which comprises administering an effective amount of an agent which blocks and/or inhibits melatonin, precursors thereof and/or metabolic products thereof and optionally light therapy to a patient in need thereof.

The present invention further provides a method for the preclinical diagnosis of a neurological or neuropsychiatric disorder associated with dopamine function which includes the step of administering melatonin to a patient suspected of having such disorder.

Melatonin is administered at a predetermined time of day to induce a mild transient form of the disorder, followed by the assessment of the efficacy of a particular therapy which blocks and/or inhibits melatonin, precursors thereof and/or metabolic products thereof.

The present invention also extends to the use of an agent which blocks and/or inhibits melatonin, precursors thereof and/or metabolic products thereof in the manufacture of a medicament for the treatment and/or prophylaxis of a neurological or neuropsychiatric is order associated with altered dopamine function.

The patient may be a human or an animal such as a domestic or wild animal, particularly an animal of economic importance.

An "effective amount" of the agent is an amount sufficient to ameleriorate and/or inhibit the neurological or neuropsychiatric disorder.

When a compound of the invention is administered to a human subject the daily dosage can normally be determined by the attending physician with the dosage generally varying according to the age, weight, and response of the individual patient, as well as the severity of the patient's symptoms. In general a suitable dose of the compound of the invention will be in the range of 0.01 to 50 mg per kilogram body weight of the recipient per day, preferably in the range of 0.5 to 10 mg per kilogram body weight per day. The desired dose is preferably presented as two, three, four, five, six or more sub-doses administered at appropriate intervals throughout the day. These sub-doses may be administered in unit dosage forms, for example, containing 1 to 500 mg, preferably 10 to 1000 mg of active ingredient per unit dosage form.

The agent may be administered for therapy by any suitable route, including oral, implant, rectal, inhalation or insulation (through the mouth or nose), topical (including buccal and sublingual), vaginal and parenteral (including subcutaneous, intramuscular, intravenous, intrastemal and intradermal). It will be appreciated that the preferred route will vary with the condition and age of the patient and the chosen agent.

The agent may be administered in the form of a composition, together with one or more pharmaceutically acceptable carriers, diluents, adjuvants and/or excipients.

Thus, according to a further aspect of the present invention there is provided a pharmaceutical or veterinary composition for the treatment and/or prophylaxis of a neurological or neuropsychiotic disorder associated with altered dopamine function which comprises an agent which blocks and/or inhibits melatonin, precursors thereof and/or metabolic products thereof in association with a pharmaceutically or veterinary acceptable carrier, diluent, adjuvant and/or excipient.

The carrier, diluent, adjuvant and/or excipient must be pharmaceutically "acceptable" in the sense of being compatible with the other ingredients of the composition and not injurious to the subject. Compositions include those suitable for oral, implant, rectal, inhalation or insulation (through the mouth or nose), topical (including buccal and sublingual), vaginal or parenteral (including subcutaneous, intramuscular, intravenous and intradermal) administration. The compositions may conveniently be presented in unit dosage form and may be prepared by methods well known in the art of pharmacy. Such methods include the step of bringing into association the agent with the carrier which constitutes one or more accessory ingredients. In general, the compositions are prepared by uniformly and intimately bringing into association the agent with liquid carriers, diluents, adjuvants and/or excipients or finely divided solid carriers or both, and then if necessary shaping the product.

Compositions of the present invention suitable for oral administration may be presented as discrete units such as capsules, sachets or tablets each containing a predetermined amount of the agent; as a powder or granules; as a solution or a suspension in an aqueous or non-aqueous liquid; or as an oil-in-water liquid emulsion or a water-in-oil liquid emulsion. The agent may also be presented as a bolus, electuary or paste.

A tablet may be made by compression or moulding, optionally with one or more accessory ingredients. Compressed tablets may be prepared by compressing in a suitable machine the agent in a free-flowing form such as a powder or granules, optionally mixed with a binder (e.g. pregelatinised maize starch, polyvinylpyrrolidone or hydroxypropyl methyl cellulose), fillers (e.g. lactose, microcrystalline cellulose or calcium hydrogen phosphate), lubricants (e.g. magnesium stearate, talc or silica), inert diluent, preservative, disintegrant (e.g. sodium starch glycollate, cross-linked povidone, cross-linked sodium carboxymethyl cellulose), surface-active or dispersing agents. Moulded tablets may be made by moulding in a suitable machine a mixture of the powdered compound moistened with an inert liquid diluent. The tablets may optionally be coated or scored and may be formulated so as to provide slow or controlled release of the agent therein using, for example, hydroxypropylmethyl cellulose in varying proportions to provide the desired release profile. Tablets may optionally be provided with an enteric coating, to provide release in parts of the gut other than the stomach.

Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid).

Compositions suitable for topical administration in the mouth include lozenges comprising the agent in a flavoured basis, usually sucrose and acacia or tragacanth gum; pastilles comprising the agent in an inert basis such as gelatin and glycerin, or sucrose and acacia gum; and mouthwashes comprising the agent in a suitable liquid carrier.

For topical application for the skin, the agent may be in the form of a cream, ointment, jelly, solution or suspension.

For topical application to the eye, the agent may be in the form of a solution or suspension in a suitable sterile aqueous or non-aqueous vehicle. Additives, for instance buffers, preservatives including bactericidal and fungicidal agents, such as phenyl mercuric acetate or nitrate, benzalkonium chloride or chlorohexidine and thickening agents such as hypromellose may also be included.

The agent may also be formulated as depot preparations. Such long acting formulations may be administered by implantation (e.g. subcutaneously or intramuscularly) or by intramuscular injection. Thus, for example, the agent may be formulated with suitable polymeric or hydrophobic materials (e.g. as an emulsion in an acceptable oil or ion exchange resins), or as sparingly soluble derivatives, for example, as a sparingly soluble salt.

Preferably, the agent is administered in the form of a polymeric implant, such as, a microsphere adapted for sustained or pulsed release to those parts of the central nervous system where dopamine is present, for example, substantial nigra, globus pallidus or nucleus caudatas.

Compositions for rectal administration may be presented as a suppository or retention enema with a suitable non-irritating excipient which is solid at ordinary temperatures but liquid at the rectal temperature and will therefore melt in the rectum to release the agent. Such excipients include cocoa butter or a salicylate.

For intranasal and pulmonary administration, the agent may be formulated as solutions or suspensions for administration via a suitable metered or unit dose device or alternatively as a powder mix with a suitable carrier for administration using a suitable delivery device.

Compositions suitable for vaginal administration may be presented as pessaries, tampons, creams, gels, pastes, foams or spray formulations containing in addition to the agent such carriers as are known in the art to be appropriate.

Compositions suitable for parenteral administration include aqueous and non-aqueous isotonic sterile injection solutions which may contain anti-oxidants, buffers, bacteriostatis and solutes which render the composition isotonic with the blood of the intended subject; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage compositions are those containing a daily dose or unit, daily sub-dose, as hereinabove described, or an appropriate fraction thereof, of agent.

The agent may also be presented for use in the form of veterinary compositions, which may be prepared, for example, by methods that are conventional in the art. Examples of such veterinary compositions include those adapted for:

(a) oral administration, external application, for example drenches (e.g. aqueous or non-aqueous solutions or suspensions); tablets or boluses; powders, granules or pellets for admixture with feed stuffs; pastes for application to the tongue;

(b) parenteral administration for example by subcutaneous, intramuscular or intravenous injection, e.g. as a sterile solution or suspension; or (when appropriate) by intramammary injection where a suspension or solution is introduced into the udder via the teat;

(c) topical application, e.g. as a cream, ointment or spray applied to the skin; or (d) intravaginally, e.g. as a pessary, cream or foam.

It should be understood that in addition to the ingredients particularly mentioned above, the compositions of this invention may include other agents conventional in the art having regard to the type of composition in question, for example, those suitable for oral administration may include such further agents as binders, sweeteners, thickeners, flavouring agents, disintegrating agents, coating agents, preservatives, lubricants and/or time delay agents.

Suitable sweeteners include sucrose, lactose, glucose, aspartaue or saccharin. Suitable disintegrating agents include corn starch, methylcellulose, polyvinylpyrrolidone, xantlan gum, bentonite, algiric acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, steric acid, sodium oleate, sodium chloride or talc. Suitable time delay agents include glyceryl monostearate or glyceryl distearate.

The invention will now be described with reference to the following Examples. These Examples are not to be construed as limiting the invention in any way.

Experimental Method

It has been suggested that lesions of the brain dopamine systems in mammalian species serve as models for a variety of neuropsyciatric disorders. When lesions are placed at various levels along the ascending dopamine pathways in the brains of experimental animals, there are alterations in dopamine function which are accompanied by both acute and prolonged changes in emotional, motoric and feeding behaviours, each of which has been attributed to a specific biochemical sequelae.

For example, alterations of central catecholamine function, particularly that of the ascending noradrenergic and dopamine systems innervating the striatum have been identified as responsible for underlying schizophrenia(30). The experimental concomitants of motor disorder can be produced in several species by lesioning the ascending dopamine system at any anatomical location extending from the midbrain cell bodies of the substantial nigra to the caudate/putamen nucleus. Depending on the species employed, this can result in loss of appetite and body weight, bradykinesia, loss of orabuccal reflex and even tremor and eventual death. The pathology of the ascending dopamine systems has also been implicated in a more subtle, neuropathology of anorexia nervosa and associated depression on several grounds.

Recent work, and the earlier work of others, reveals that there are many parallels between the clinical syndrome of anorexia nervosa and the experimental model with altered dopamine function employed by the present inventors. Such parallels include i) the mutualisation of food ii) increased activity in the presence of severe energy store depletion and emaciation; iii) increased motivation toward food with reduced food intake and body weight; iv) hypothermia; and v) altered dopamine function, in particular, the similarities between 6-OHDA induced anorexia and that occurring after amphetamine.

At appropriate concentrations, the neurotoxin 6-hydroxydopamine (hereinafter referred to as "6-OHDA") produces specific and permanent lesions of brain monoamines. Intracranial injections of this compound were used in the Examples to produce models of movement disorders such as Parkinson's disease and schizophrenia. Bilateral lesions of the nigrostriatal pathway result in a vegetative, akinetic syndrome characterised by lack of voluntary movement, hunched posture and body weight loss concomitant with severe adipsia and aphagia. As a check on the results, 1-methyl-4-phenyl-1,2,3,6-tetrahydropyridine (hereinafter referred to as "MPTP") which is also known to cause Parkinsonism by mechanisms similar to that of 6-OHDA was administered as a second animal model.

In humans, MPTP was first synthesised as a herbicide, similar to paraquat, and workers exposed to large quantities developed irreversible Parkinsonism, not unlike the idiosyncratic form of the disease. Then, MPTP was used in the illicit drug market to "cut"morphine and give it an increased boost (e.g. by euphoria). This use resulted in the first patient to be misdiagnosed as a schizophrenic and maintained on antipsychotic therapy for three months. Over time many addicts exposed to MPTP developed Parkinson symptoms.

EXAMPLE 1

The natural release of melatonin may be involved in the development of motor impairment. One method of inhibiting endogenous melatonin release is by placing animals in an environment where they are exposed to bright, constant light. One group of animals was placed in an environment with constant light (minimum intensity=150 lux) two weeks after undergoing cannulation of the PLH described as follows:

After several days of control observations, all animals were injected bilaterally with 2 μl of an 8 μg/μl solution of 6-OHDA. Body weight was measured each day just after the onset of the light cycle and motor performance was measured by assessing the performance of animals in the open field and on three tests routinely used to assess motor function. Open field activity was measured in a PVC box fitted with infrared sensors. The number of beams broken during a 10 minute test period was registered. The three reflex tests employed were latency to retract a limb elevated 25 cm above the surce of the test area, latency to step up or down from a raised platform when the rear torso was elevated 30 cm above the test area surface and latency to step outside a prescribed area. All tests had an optimal latency cut off point of 30 s and were based on extensive validation, use and experience.

A second group of cannulated animals was placed in an environment with a 12 hr light/12 hr dark cycle. Afler 20 days of control observations of body weight and motor function, the animals were injected with 6-OHDA as described below in Example 3. Body weight was measured each day after 6-OHDA for 24 days and motor performance was measured on days 2, 4, 14 15.

Figure 1:
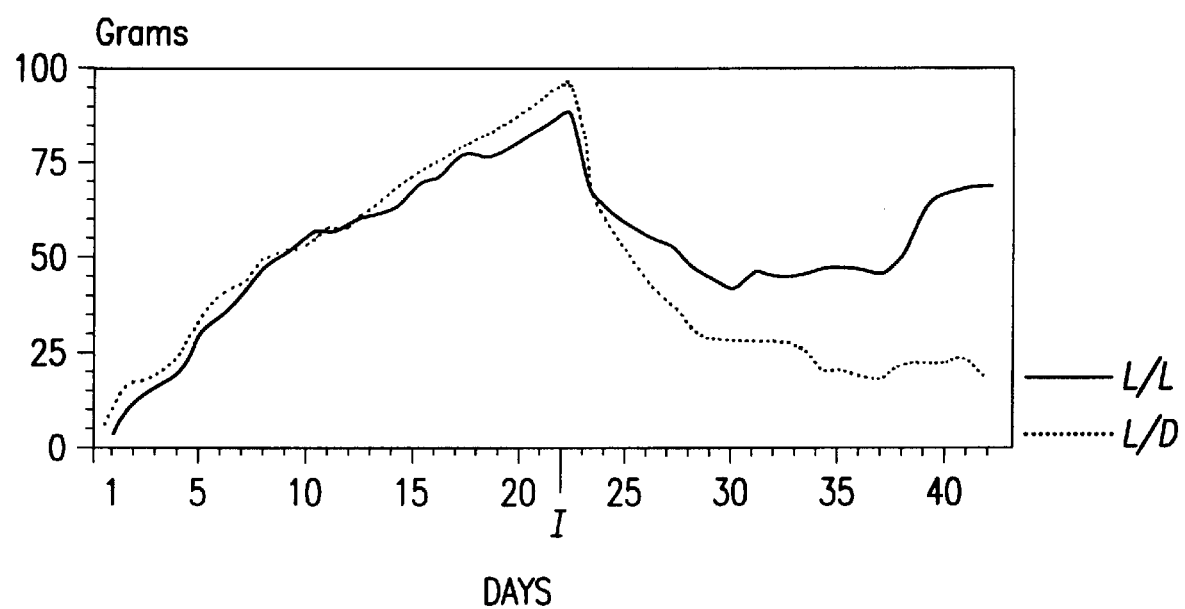
FIG. 1 is a graph showing the effect constant light exposure on body weight regulation in rats receiving intracerebral injections of 6-OHDA to induce experimental anorexia and body weight loss in which injections were administered on the day marked "I" and body weight was plotted with respect to the daily cumulative change for each group. (LL=24 h exposure to light; LD=12 h light, 12 h dark cycle.)

FIG. 1 shows the daily cumulative change in body weight for animals housed in either L/L or L/D was similar for the first 22 days of control observation before the injection of 6-OHDA. After this time, those animals housed in L/D showed a progressively more severe drop in body weight than those in L/L ($p=0.001$). Recovery commenced 10 days after 6-OHDA injection in L/L animals while those in L/D were still loosing weight at day 44.

Figure 2A:
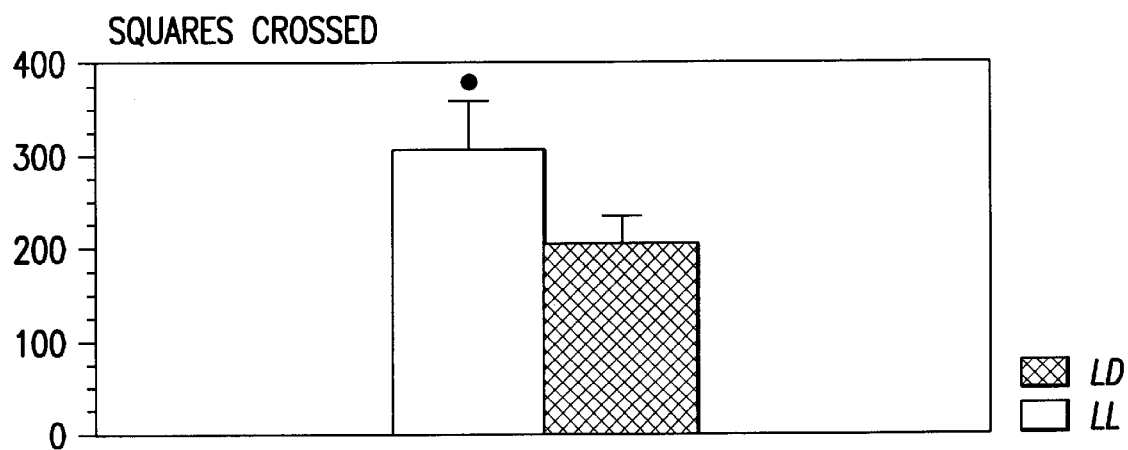
FIG. 2A is a graph showing the effect of constant light exposure on overall locomotion during several 10 minute test sessions in an infrared activity chamber in rats receiving intracerebral injections of 6-OHDA and measurements were taken during the light and dark phases of the light cycle. (LL=24 h exposure to light; LD=12 h light, 12 h dark cycle.)
Figure 2B:
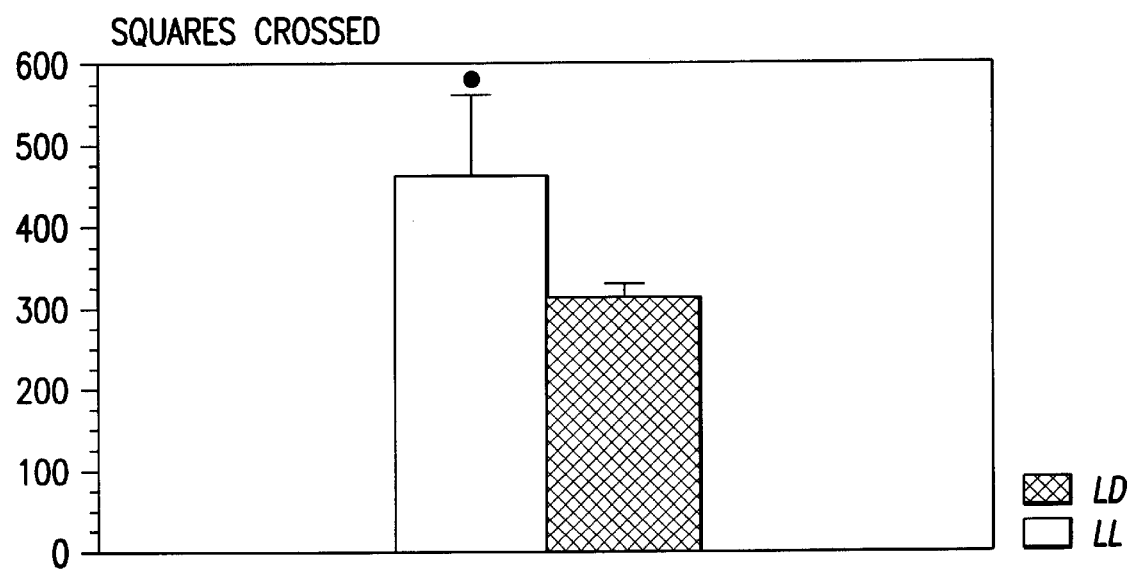
FIG. 2B is a graph showing the effect of constant light exposure on locomotion during 10 minute test sessions in an infrared activity chamber within 4 days after rats received intracerebral injections of 6-OHDA and measurements were taken during the light and dark phases of the light cycle. (LL=24 h exposure to light; LD=12 h light, 12 h dark cycle.)

The motor activity on all tests of motor function were significantly different between the two groups. In FIG. 2A, impairment in the open filed was significantly less severe in L/L animals injected with 6-OHDA than those housed in L/D ($p=0.05$). As shown in FIG. 2A, when tested during the recovery phase of the experiment, the performance of L/L animals was significantly better than that of L/D animals ($p=0.035$).

Figure 3:
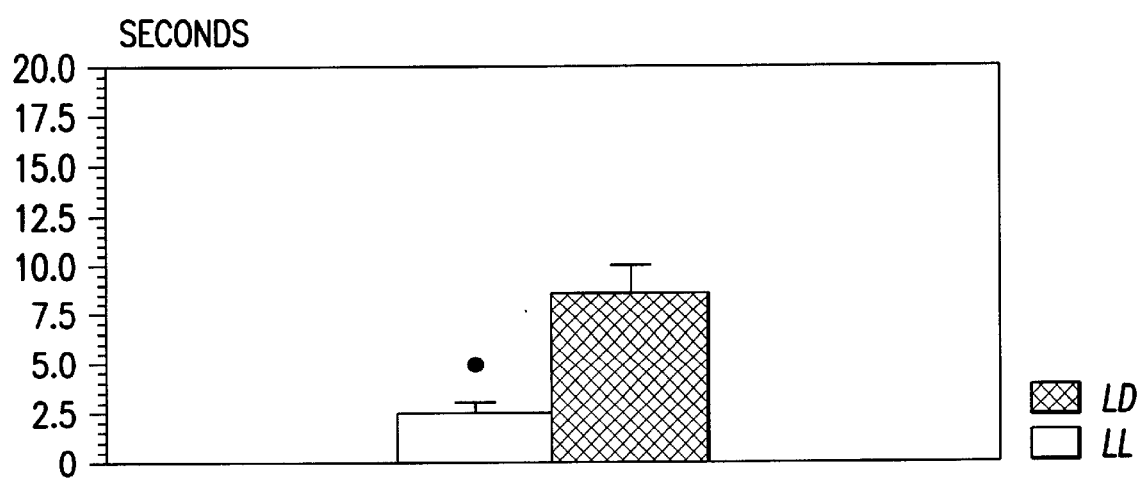
FIG. 3 is a graph showing the effect of constant light exposure on the ability to retract a limb during several measurement sessions during the light and dark phases of the light cycle after rats received intracerebral injections of 6-OHDA. (LL=24 h exposure to ight; LD=12 h light 12 h dark cycle.)
Figure 4:
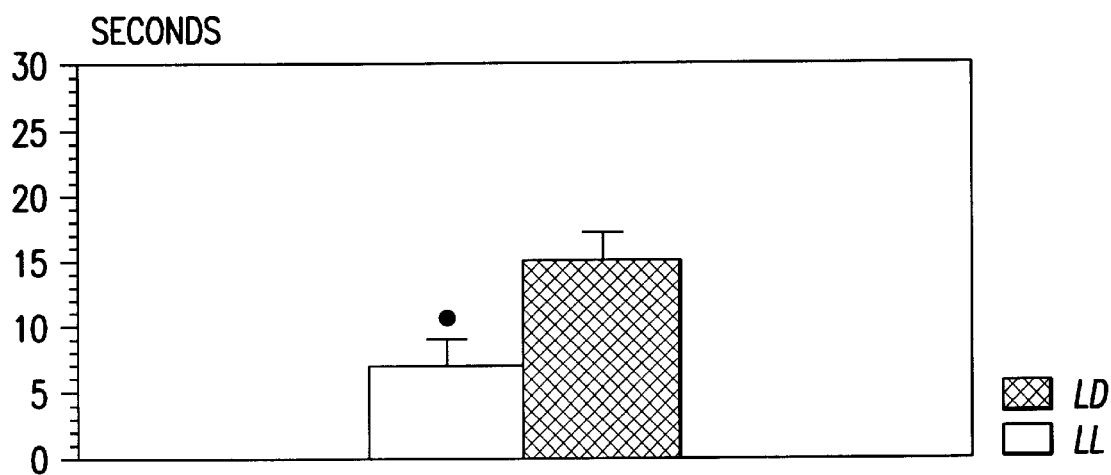
FIG. 4 is a graph showing the effect of constant light exposure on the ability to step down during several measurement sessions during the light and dark phases of the light cycle afterrats received intracerebral injections of 6-OHDA. (LL=24 h exposure to light; LD=12 h light, 12 h dark cycle.)
Figure 5:
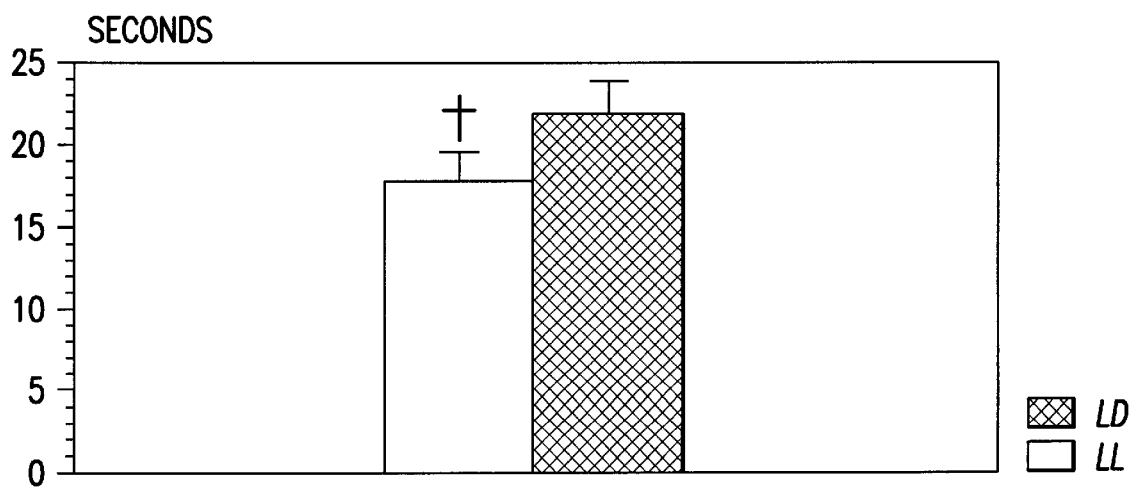
FIG. 5 is a graph showing the effect of constant light exposure on the ability to ambulate during several measurement sessions during the light and dark phases of the light cycle after rats received intracerebral injections of 6-OHMA. (LL=24 h exposure to light; LD=12 h light, 12 h dark cycle.)

Latency to retract a limb (FIG. 3) was only slightly increased by 6-OHDA animals if they were housed in L/L while those housed in L/D showed the classical severe impairment of this reflex. The performance of L/L animals was significantly better than in L/D animals ($p=0.000$). Latency to Step was similarly affected with L/L animals showing slight impairment while those in L/D were severely impaired (FIG. 4; $p=0.00?9$). Latency to ambulate was only marginally affected by exposure to L/L but with a significant trend by L/L animals in the predicted direction (FIG. 5; $p=0.089$).

Figure 6:
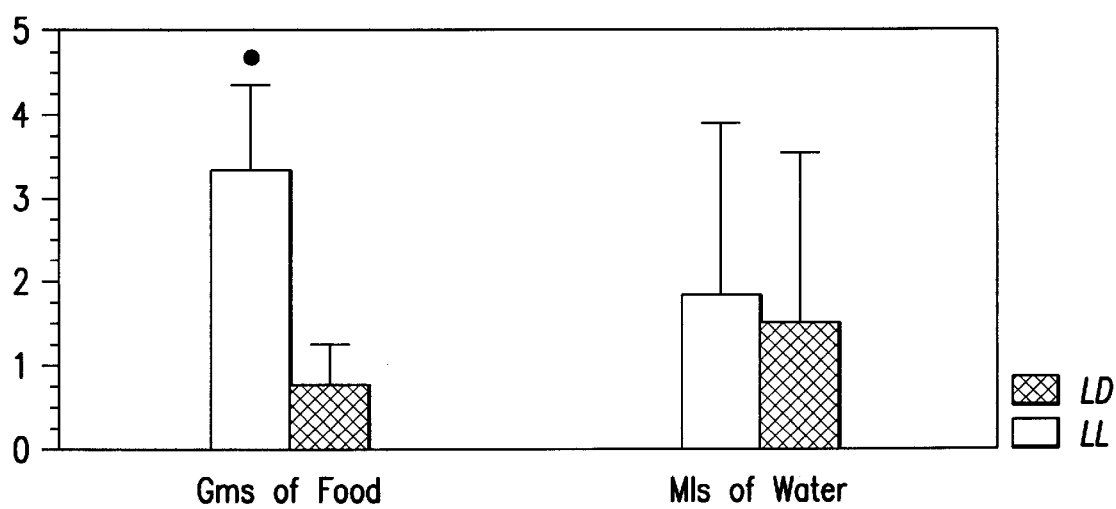
FIG. 6 is a graph showing the effect of constant light(LL) compared with a cycle of 12 hr light/ 12 hr dark (L/D) on a 3 hr food and water intake test in animals 6 days after they were injected with intra-cerebral 6-OHDA.

Animals housed in L/L lived longer than those in L/D. As shown in FIG. 6, the food intake of animals in the L/L group was significantly higher than that of animals in L/D dunng a 3 hour test ($p=0.025$) while water intake was similar in both groups.

EXAMPLE 2

In order to remove the principle source of endogenous melatonin, the pineal gland was surgically removed under anaesthesia. SHAM rats served as controls which were subjected to surgery including anaesthesia, incision, craniotomy, puncturing of the sinus and bleeding, but the pineal was not disturbed. Body weight was measured each day for the course of the experiment and motor reflex control was measured on days 2, 4, 14, 15. 6-OHDA injections were administered as specified in Example 3 except that the injections were made acutely without implanting permanent cannulae, on the days indicated.

Figure 7:
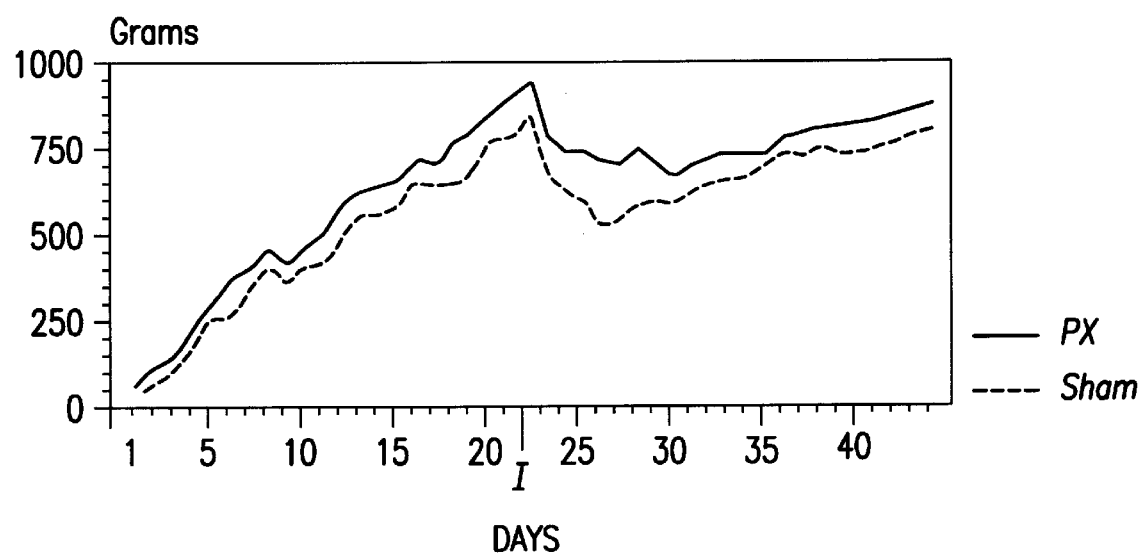
FIG. 7 is a graph showing the effect of pinealectomy on body weight regulation in rats receiving intra-cerebral injections of 6-OHDA to induce experimental anorexia and body weight loss in which injections were administered on the day marked "I" and body weight was plotted with respect to the daily cumulative change for each group. (PX= pinealectomized animals and SHAM=animals were subjected to control surgery without extracting the pineal.)
Figure 8A:
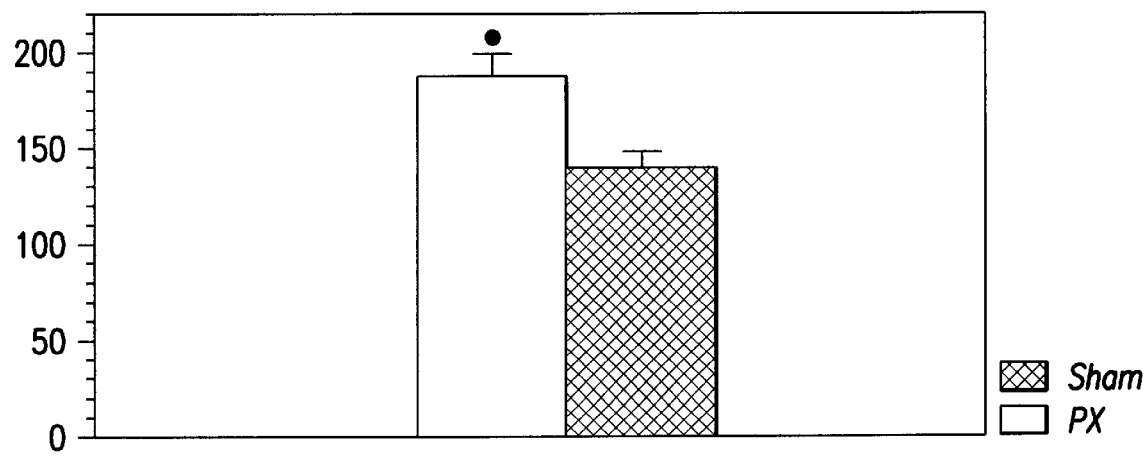
FIG. 8A is a graph showing the effect of pinealectomy on overall locomotion during several 10 minute test sessions in an infrared activity chamber in rats receiving intracerebral injections of 6-OHDA and measurements were taken during the light and dark phases of the light cycle. (PX= pinealectomized animals and SHAM=animals were subjected to control surgery without extracting the pineal.)
Figure 8B:
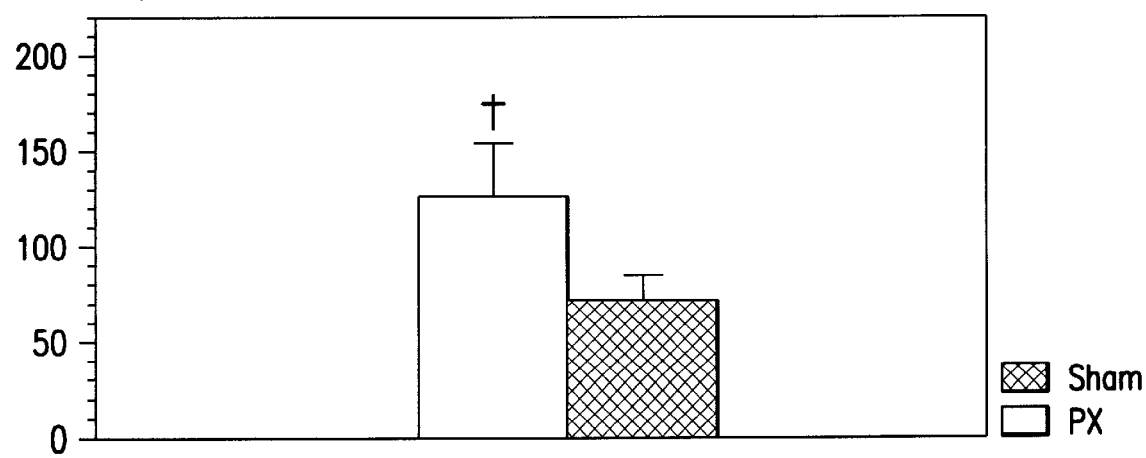
FIG. 8B is a graph showing the effect of pinealectomy on locomotion during 10 minute test sessions in an infrared activity chamber within 4 days after rats received intracerebral injections of 6-OHDA and measurements were taken during the light and dark phases of the light cycle. (PX= pinealectomnized animals and SHAM=animals were subjected to control surgery without extracting the pineal.)
Figure 9:
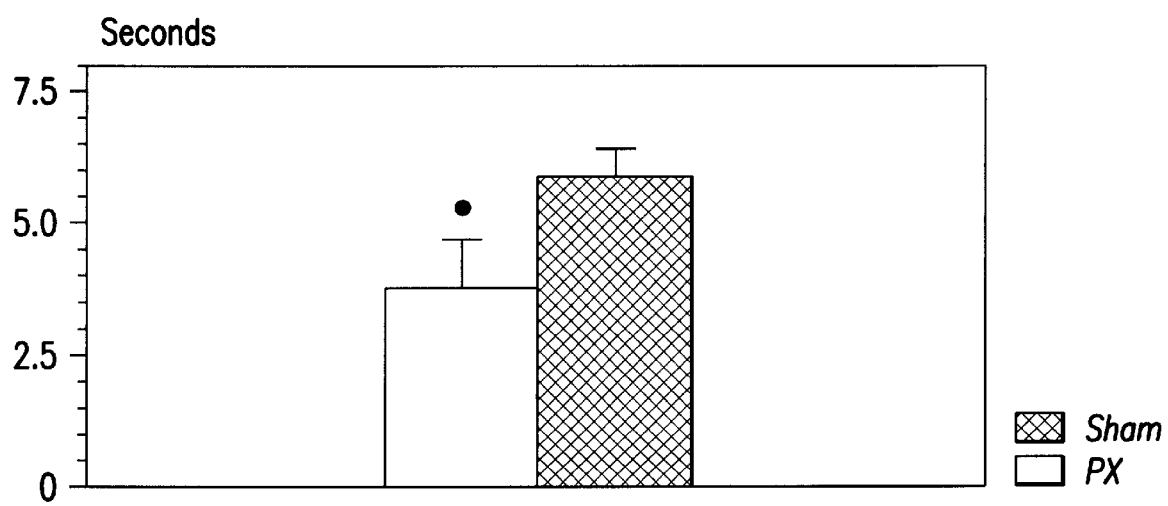
FIG. 9 is a graph showing the effect of pinealectomy on the ability to retract a limb during several measurement sessions after rats received intracerebral injections of 6-OHDA and measurements were taken during the light and dark phases of the light cycle. (PX=pinealectomized animals and SHAM=animals were subjected to control surgery without extracting the pineal.)
Figure 10:
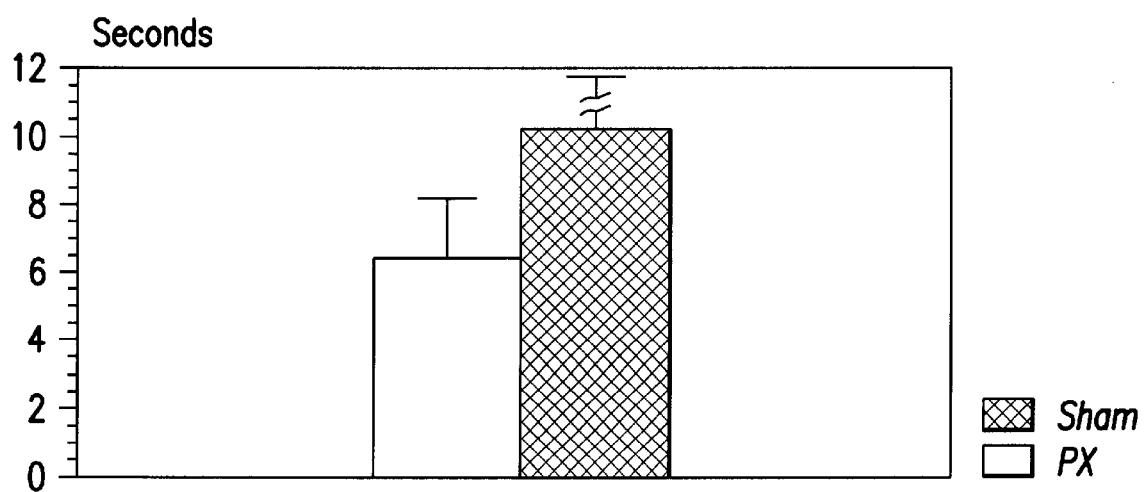
FIG. 10 is a graph showing the effect of pinealectomy on the ability to step down during several measurement sessions after rats received intracerebral injections of 6-OHDA and measurements were taken during the light and dark phases of the light cycle. (PX=pinealectomized animals and SHAM=animals were subjected to control surgery without extracting the pineal.)
Figure 11:
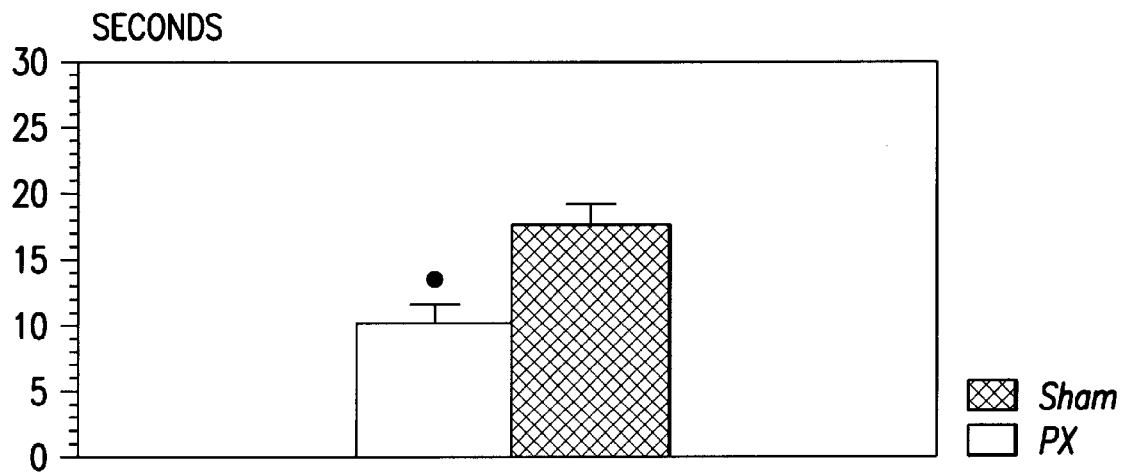
FIG. 11 is a graph showing the effect of pinealectomy on the ability to ambulate during several measurement sessions after rats received intracerebral injections of 6-OHDA and measurements were taken during the light and dark phases of the light cycle. (PX=pinealectomized animals and SHAM=animals were subjected to control surgery without extracting the pineal.)
Figure 12:
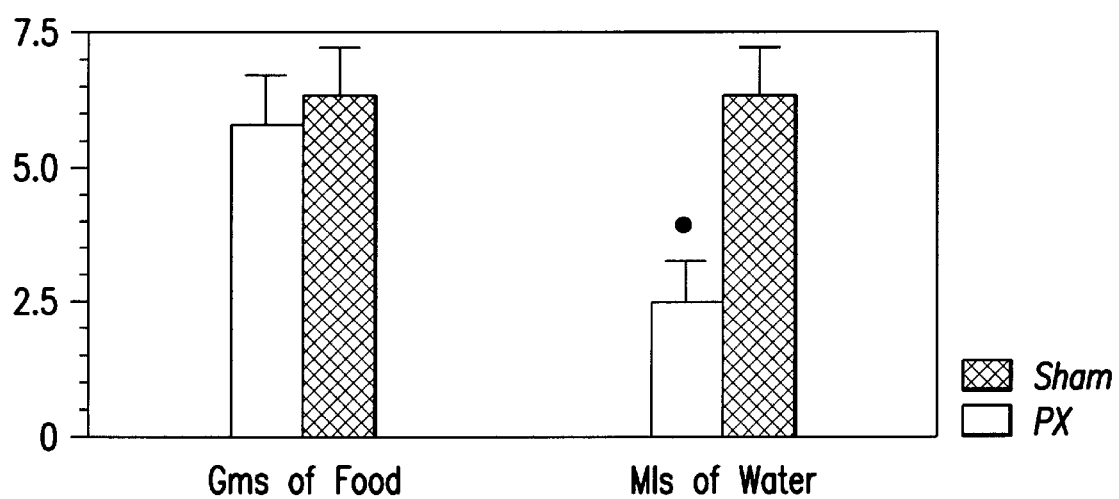
FIG. 12 is a graph showing the effect of pinealectomy compared with animals subjected to control surgery without extracting the pineal on a 3 hr food and water intake test in animals 6 days after they were injected with intra-cerebral 6-OHDA and measurements were taken during the first 3 hr period after the onset of the dark cycle.

As shown in FIG. 7, the body weight of animals with PZ was similar to the SHAM animals until they received an intracerebral injection of 6-OHDA. Both groups then lost body weight at a comparable rate on the first 2 days after injection, but then the PX animals increased their weight on days 23 to 30 while the SHAM operated animals continued to decline during that time and the difference was significant (p=0.05). FIG. 8A shows that the open field performance of PX animals was significantly better (p=0.045) than that of their SHAM operated counterparts at both times of measurement. PX animals also showed significant trend toward better performance during the test sessions than the SHAM animals (FIG. 8B; p=0.063).

Figure 13:
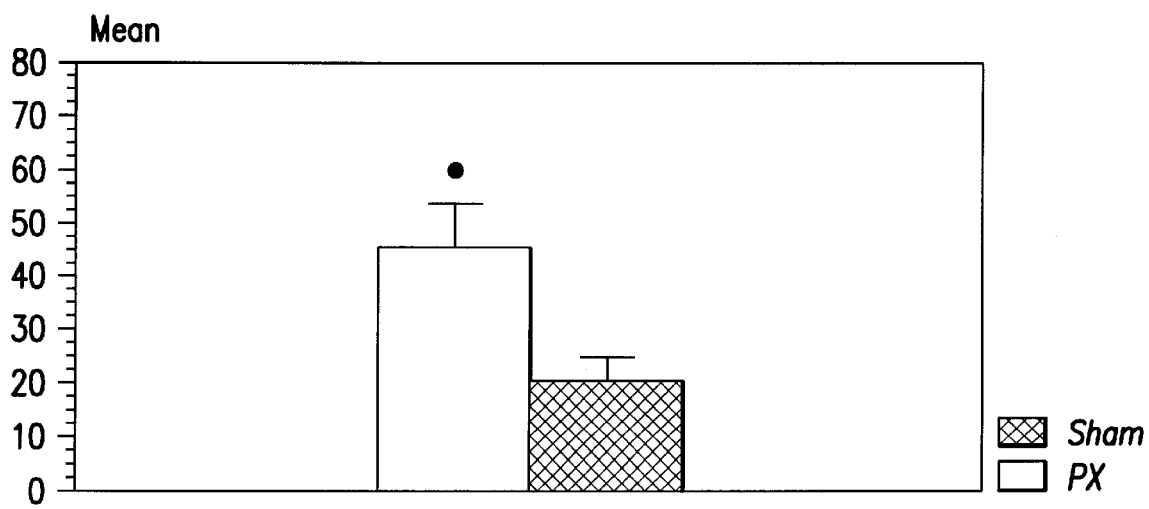
FIG. 13 is a graph showing the effect of pinealectomy on the tendency of rats to walk into the centre squares of an infrared open field (Athigmotaxis) after receiving intracerebral injections of 6-OHDA and measurements were taken during the light phase of the light cycle. (PX= pinealectomized animals and SHAM=animals were subjected to control surgery without extracting the pineal.)

As shown in FIG. 13 thigmotaxis, or the tenancy of animals to avoid movement into the centre squares of an open field, was also reduced by pinealectomy. Pinealectomy reduced the associated anxiety resulting in significantly increased movement as compared to SHAM operated controls (p=0.019).

EXAMPLE 3

In order to produce a sustained central release of melatonin, Regulin® pellets were implanted into the left cerebral ventricle of rats at the time of cannulation of the posterior, lateral hypothalamus (PLH). Control rats were implanted with inert nylon pellets of the same dimensions. This method of melatonin administration was chosen on the basis of studies which demonstrated that peripheral injection produced a mild impairment of motor function which was possible because the injection of a bolus does not approximate the low sustained release characteristics of natural release. Animals were cannulated and tested as described in Example 1.

Figure 14:
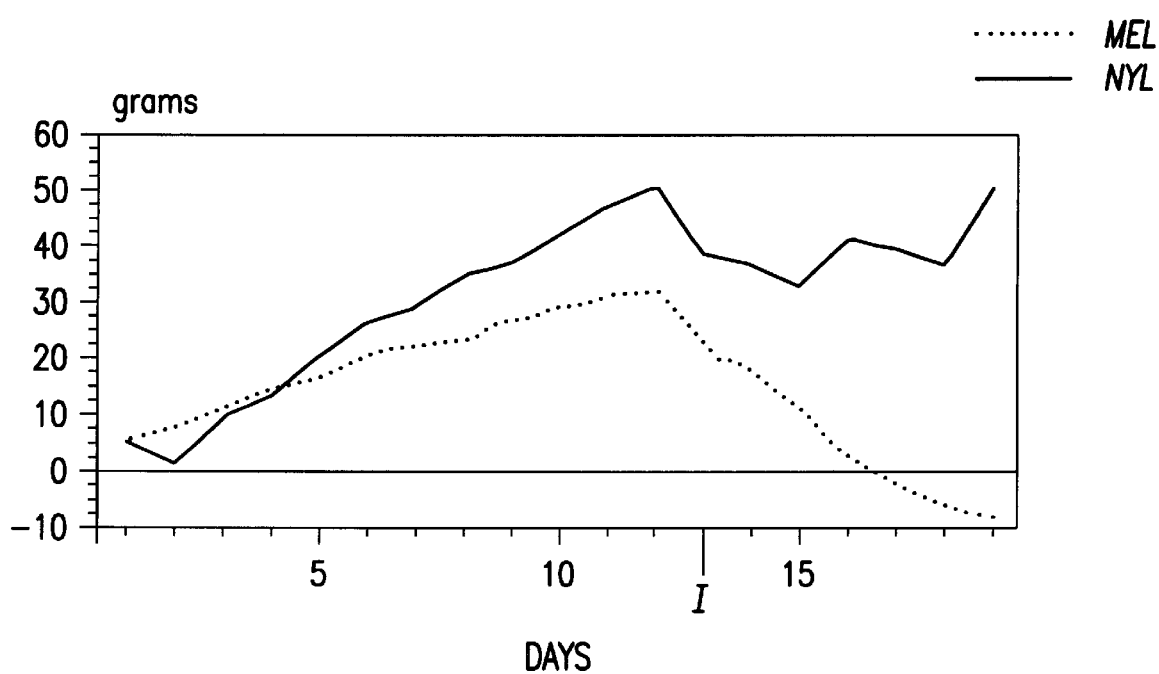
FIG. 14 is a graph showing the effect of intracerebroventricular implants of melatonin on body weight regulation in rats receiving intra-cerebral injections of 6-OHDA to induce experimental anorexia and body weight loss in which injections were administered on the day marked "I" and body weight was plotted with respect to the daily cumulative change for each group. (Mel=Melatonin and Nyl=Nylon.)

As shown in FIG. 14, the animals implanted with nylon pellets displayed a progressive reduction in body weight for the first four days after 6-OHDA injection and then spontaneous recovery commenced similar to that seen in animals implanted with melatonin. However, animals with melatonin implants showed a more sever loss of body weight on a daily basis from day 16 to the end of the experiment and this impairment was significantly greater than in nylon implanted animals in this four day period (p=0.0143).

Figure 15A:
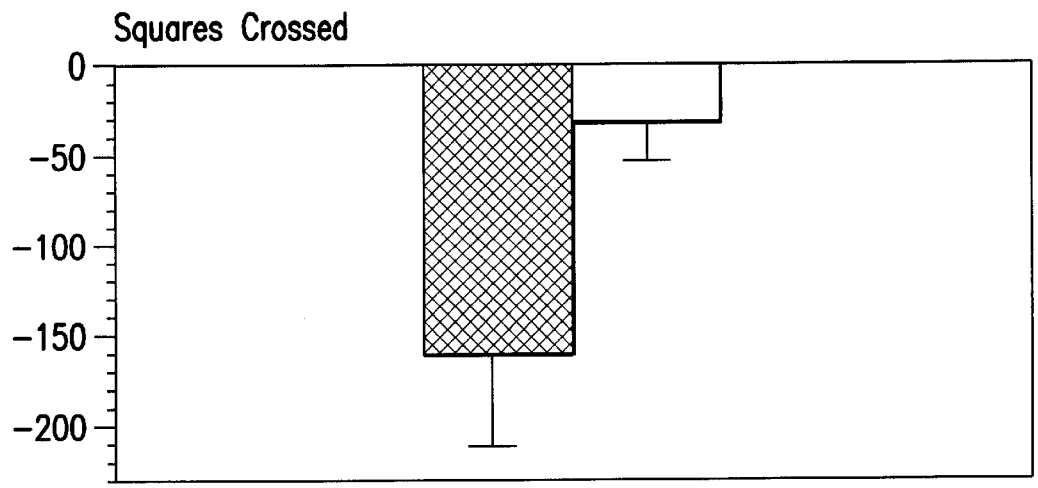
FIG. 15A is a graph showing the effect of intracerebroventricular implants of melatonin on change in locomotion during 10 minute test sessions in an infrared activity chamber in rats within 5 days after receiving intracerebral injections of 6-OHDA and measurements were taken during the light and dark phases of the light cycle. (Mel=Melatonin and Nyl=Nylon.)
Figure 15B:
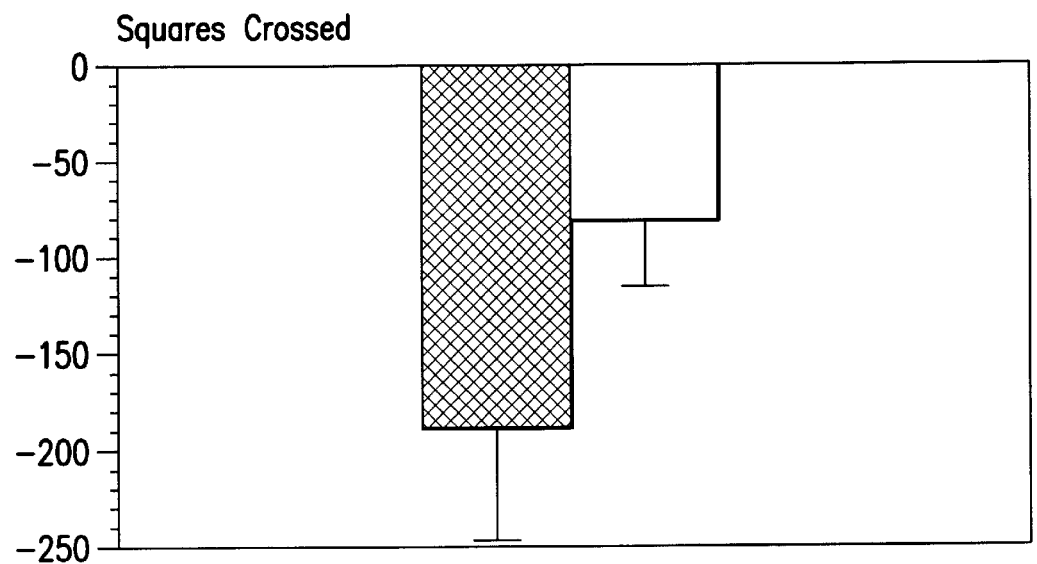
FIG. 15B is a graph showing the effect of intracerebroventricular implants of melatonin on change in locomotion during 10 minute test sessions in an infrared activity chamber 5 days after rats received intracerebral injections of 6-OHDA and measurements were taken during the light phase of the light cycle. (Mel=Megatonin and Nyl=Nylon.)
Figure 16:
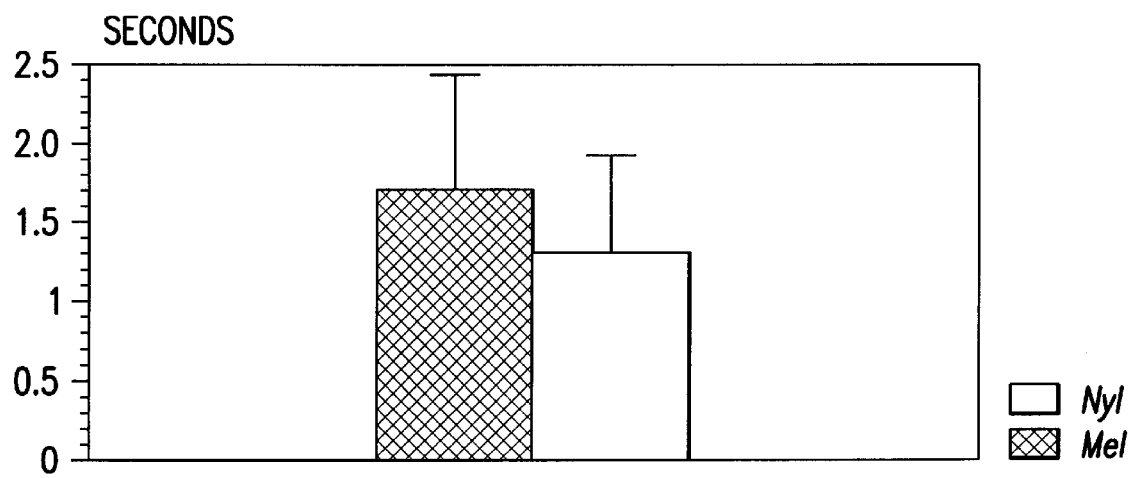
FIG. 16 is a graph showing the effect of intracerebroventricular implants of melatonin on the ability to retract a limb during the test night measurement session during the dark phase of the light cycle after rats received intracerebral injections of 6-OHDA (Mel=Melatonin and Nyl=Nylon.)
Figure 17:
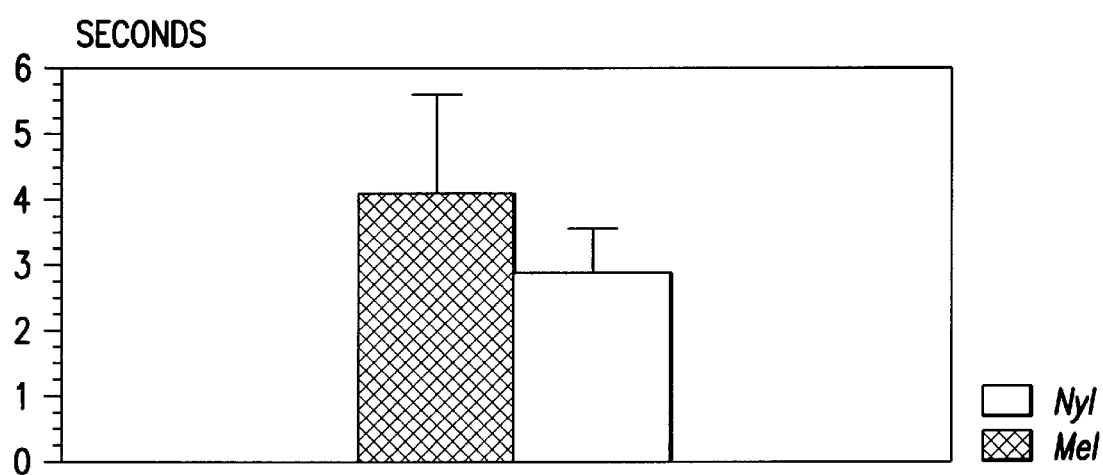
FIG. 17 is a graph showing the effect of intracerebroventricular implants of melatonin on the ability to step down during the test night measurement session during the dark phase of the light cycle after rats received intracerebral injections of 6-OHDA. (Mel=Melatonin and Nyl=Nylon.)
Figure 18:
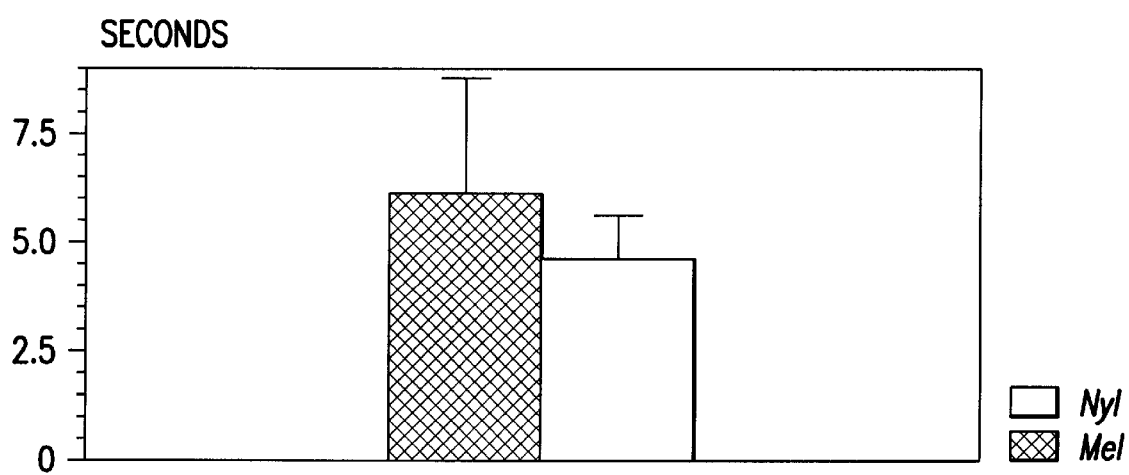
FIG. 18 is a graph showing the effect of intracerebroventricular implants of melatonin on the ability to ambulate during the test night measurement session during the dark phase of the light cycle after rats received intracerebral injections of 6-OHDA. (Mel=Melatonin and Nyl=Nylon.)

As shown in FIGS. 15A and B, the overall change in open field performance and that occurring during the test session was significantly worse in animals implanted with melatonin (p=0.0022). The animals implanted with melatonin displayed a reduction in open field performance which was more than twice as much as the animals implanted with inert nylon. The performance of the animals implanted with melatonin on the 3 motor tests was also slower than the animals implanted with nylon although not significant (FIGS. 16–18o).

EXAMPLE 4

Animals in this study were again pinealectomnized or subjected to the SHAM operation. Four to eight weeks after the pinealectomy all animals received intraperitoneal injections of MPTP as described in Example 5. Body weight was measured for several days before and 4 days after MPTP. Performance on all motor tests was measured 1 hr and 48 hrs after MPTP administration.

Figure 19A:
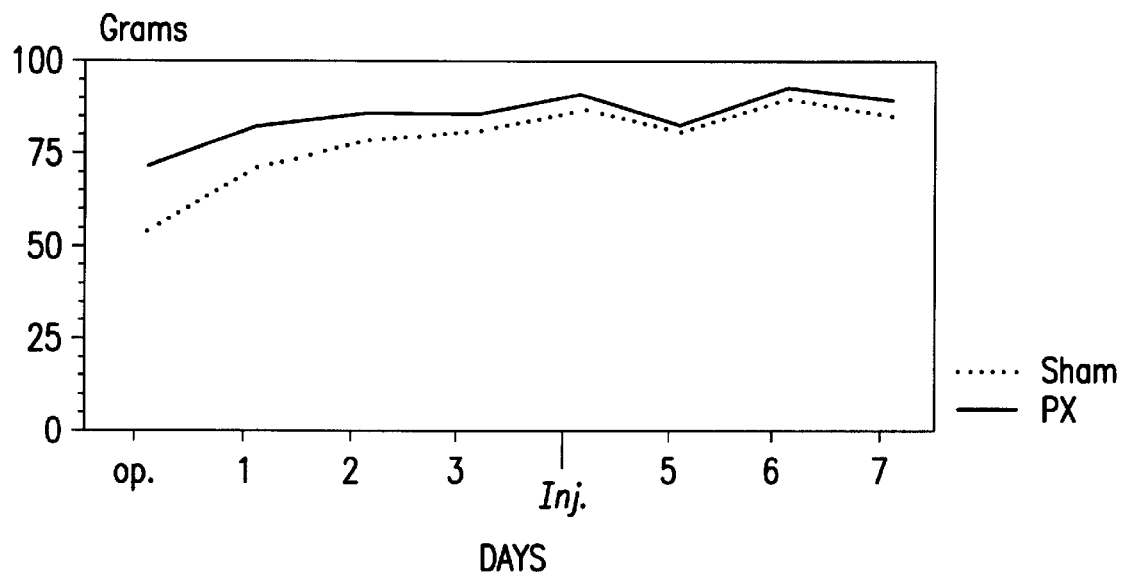
FIGS. 19A and 19B are grphs showing the effect of pinealectomy on body weight regulation in rats receiving an intraperitoneal injection of MPTP to induce experimental anorexia and body weight loss in which injections were administered on the day marked "inj." and body weight was plotted with respect to the daily cumulative change for each group. (PX=pinealectomized animals and SHAM=animals were subjected to control surgery without extracting the pineal.)
Figure 19B:
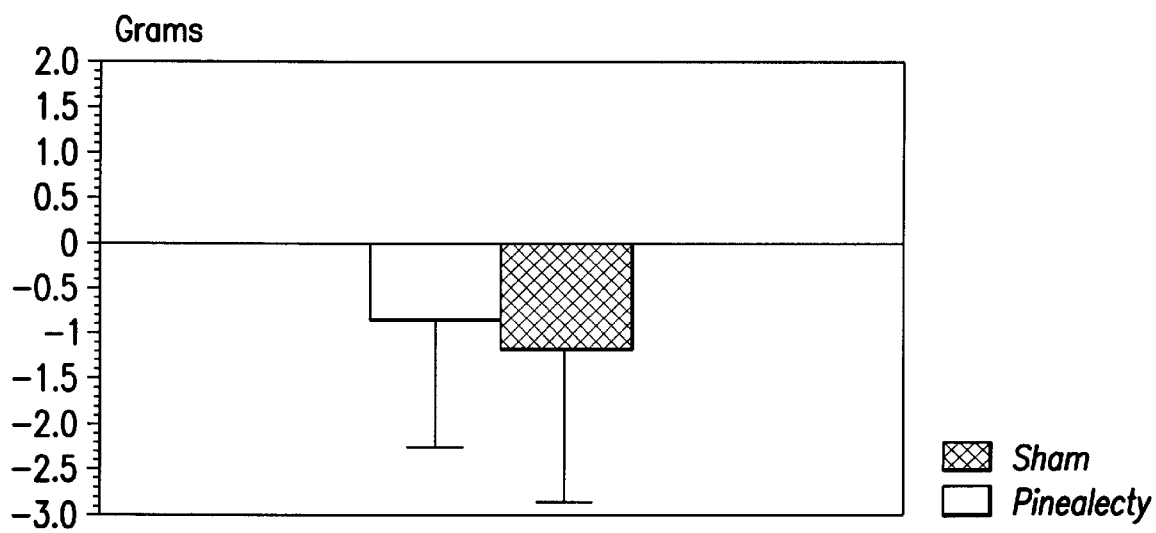

As shown in FIGS. 19A and B, PX animals regulated their body weight at a level slightly higher than that of SHAM operated controls. Furtherrnore, they also lost slightly less weight after MPTP injection than their SHAM operated counterparts, but this difference was not significant.

Figure 20:
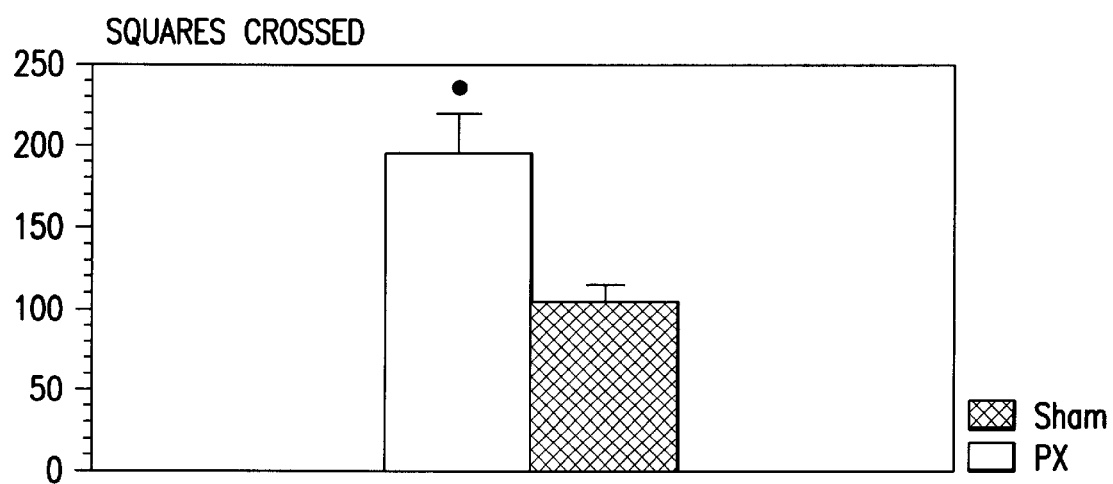
FIG. 20 is a graph showing the effect of pinealectomy on overall locomotion during several 10 minute test sessions in an infrared activity chamber at 1 and 48 h after rats received an intraperitoneal injection of MPTP and measurements were taken during the light phase of the light cycle. (PX= pinealectornized animals and SHAM=animals were subjected to control surgery without extracting the pineal.)
Figure 21A:
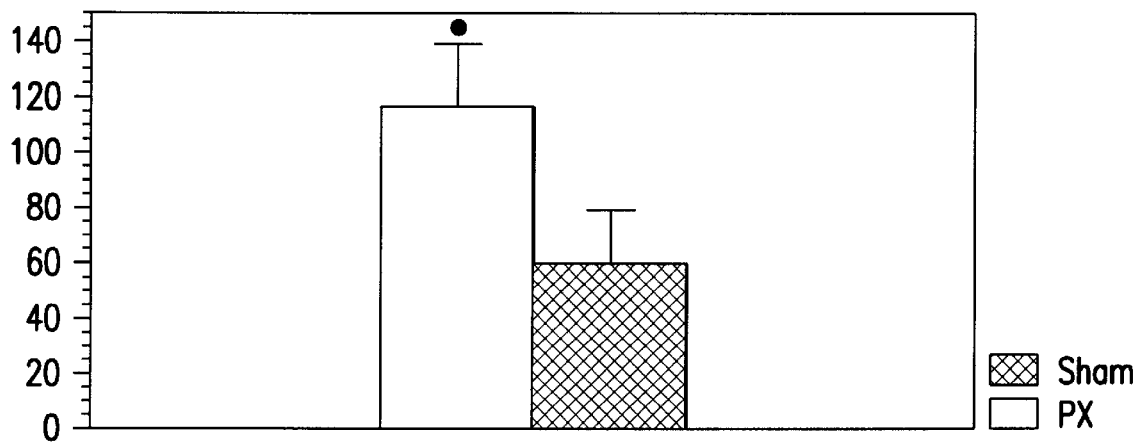
FIG. 21A is a graph showing the effect of pinealectomy on locomotion during a 10 minute test sessions in an infrared activity chamber at 1 h after rats received an intraperitoneal injection of MPTP and measurements were taken during the light phase of the light cycle. (PX=pinealectomized animals and SHAM=animals were subjected to control surgery without extracting the pineal)
Figure 21B:
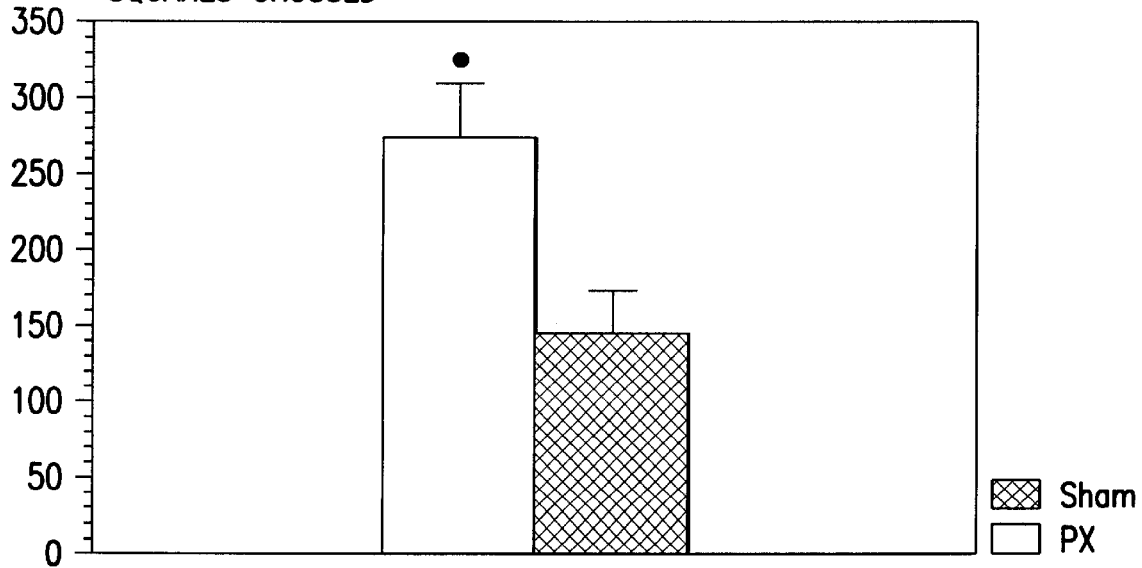
FIG. 21B is a graph showing the effect of pinealectomy on locomotion during 10 minute test sessions in an infrared activity chamber during recovery at 48 h after rats received intraperitoneal injection of MPTP and measurements were taken during the light phase of the light cycle. (PX= pinealectomized animals and SHAM=animals were FIG. 22A is a graph showing the effect of intracerebroventricular implants of melatonin on body weight regulation in rats receiving intraperitoneal injections of MPTP to induce experimental anorexia and body weight loss in which injections were administered on the day marked "inj." and body weight was plotted with respect to the daily cumulative change for each group. (Mel=Melatonin and Nyl=Nylon.)

FIG. 20 shows that at 1 hr after MPTP treatment animals pinealectomized were more active than SHAM operated controls (p=0.0051). Test performance was significantly better in PX animals in the open field (FIG. 21A; p=0.0354) and PX animals recovered quicker than SHAMs (FIG. 21B; p=0.0114).

EXAMPLE 5

The rats were implanted with intracerebral melatonin pellets or inert nylon as described in Example 3 with the exception that they were not implanted with intrahypothalamic cannulae. After the control performance was assessed, all animals received intraperitoneal injections of MPTP on day 4 (7 mg/kg/i.p.). Given that the effects of MPTP are less prolonged and traumatic than 6-OHDA, this provided an opportunity to study the phenomenon of recovery. Body weight was measured daily and motor performance was measured 1 h, and 2 days after injection.

Figure 22A:
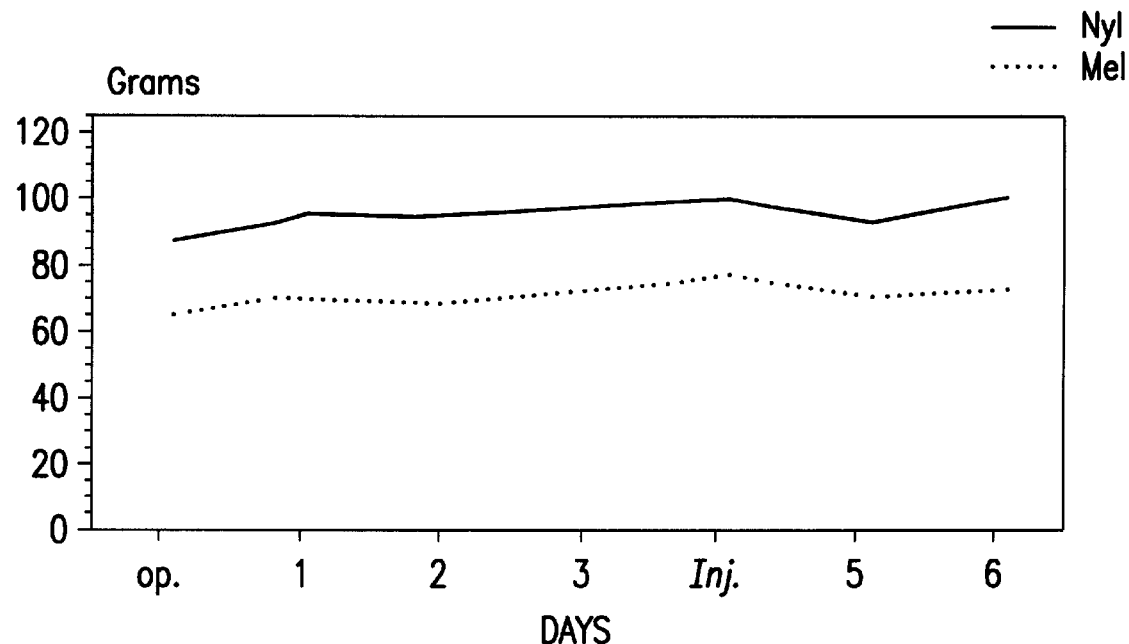
FIG. 22B is a graph showing the effect of intracerebroventricular implants of melatonin on the change in body weight in rats receiving intraperitoneal inj:ections of MPTP to induce experimental anorexa and body weight loss in which injections were admirnstered on the day marked "inj." and body weight was plotted with respect to the daily cumulative change for each group. (Mel=Melatonin and Nyl=Nylon.)
Figure 22B:
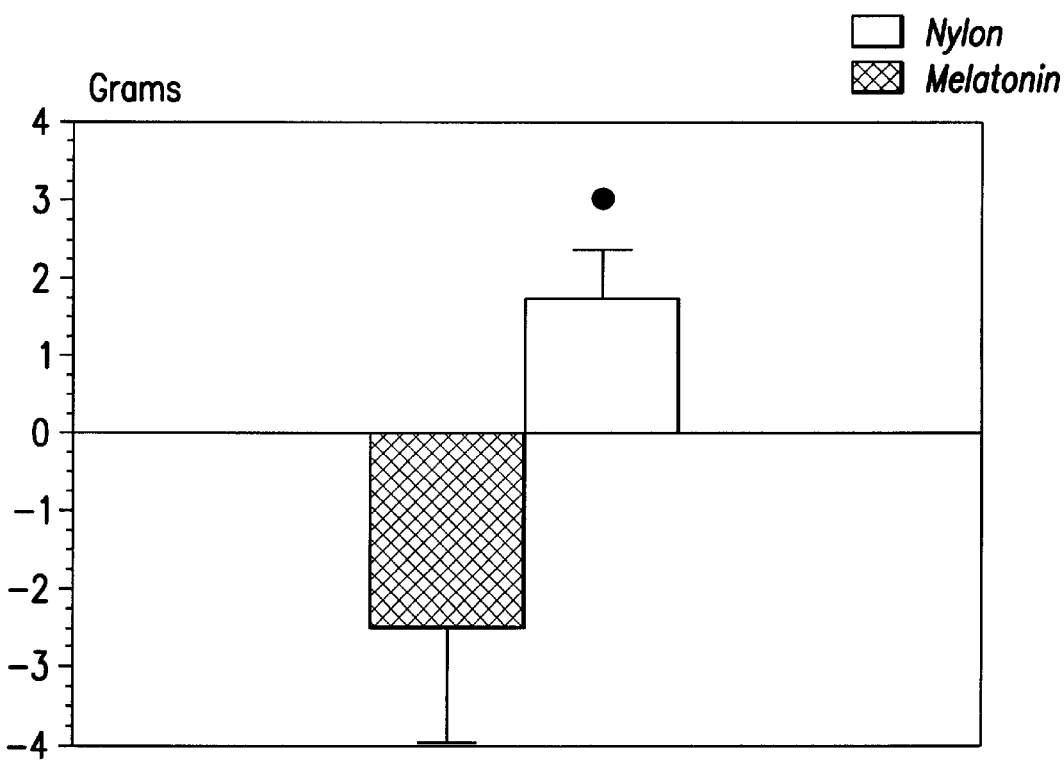
Figure 23A:
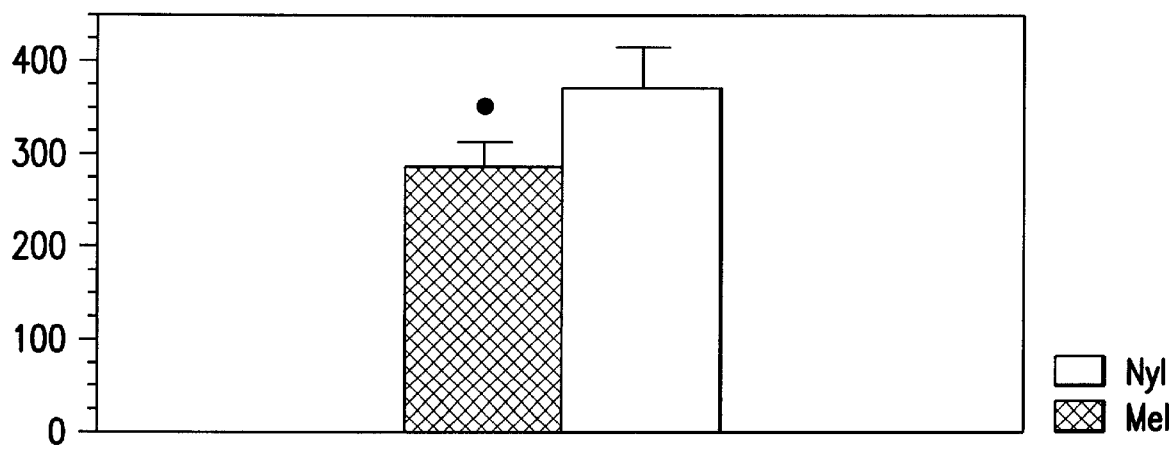
FIG. 23A is a graph showing the effect of intracerebroventricular implants of melatonin on overall locomotion during 10 minute test sessions in an infrared activity chamber in rats within 4 days after receiving intracerebral injection of MPTP and measurements were taken during the light and dark phases of the light cycle . (Mel=Melatonin and Nyl=Nylon.)
Figure 23B:
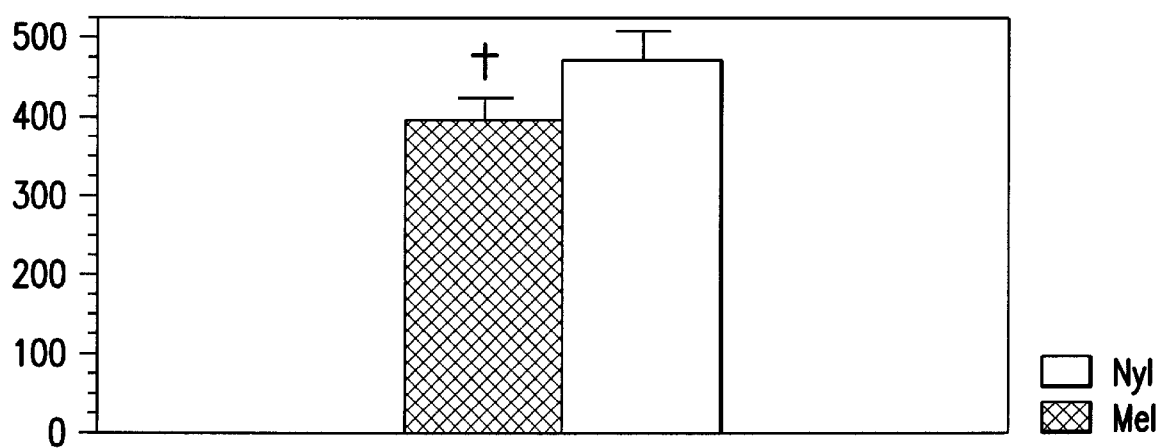
FIG. 23B is a graph showing the effect of intracerebroventricular implants of melatonin on locomotion during the dark phase of the light cycle during 10 minute test sessions in an infrared activity chamber within 4 days after rats received intraperitoneal injection of NPTP. (Mel=Melatonin and Nyl=Nylon.)
Figure 24:
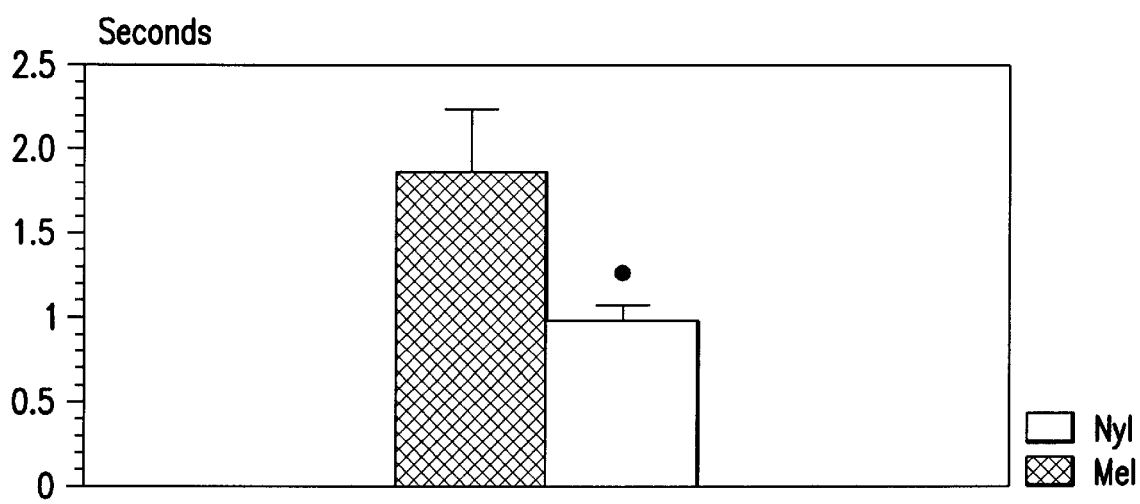
FIG. 24 is a graph showing the effect of intracerebroventricular implants of melatonin on the ability to step down during the dark phase of the light cycle within 4 days after rats received intraperitoneal injection of MPTP. (Mel= Melatonin and NYL=Nylon).

As shown in FIG. 22A, animals implanted with melatonin did not gain as much weight during the time of observation as those implanted with inert nylon. The difference in rate of weight gain was reduced after the injection of MPTP and this difference is shown in FIG. 22B (p=0.0201) and was significant. As shown in FIG. 23A and B, the implantation of melatonin pellets increased the motor impairment seen after MPTP as compared to those animals implanted with nylon (overall performance p=0.0344night perfonmance trend, p=0.0638). As shown in FIG. 24 the animals with melatonin implants displayed a significant decrement in the ability to step when assessed during the night (p=0.0238).

EXAMILE 6

One patient, diagnosed 3 years earlier with Parkinson's disease was exposed to bright light therapy (1500 lux) for two, 1 hour sessions per day, one before retiring and one immediately upon arising to antagonise melatonin secretion. This patient was also prescribed 50 mg of the β-noradrenergic antagonist, Atenolol, before going to bed. The patients performance on motor tests and her body weight were measured before treatment commenced and 2 weeks later.

Figure 25:
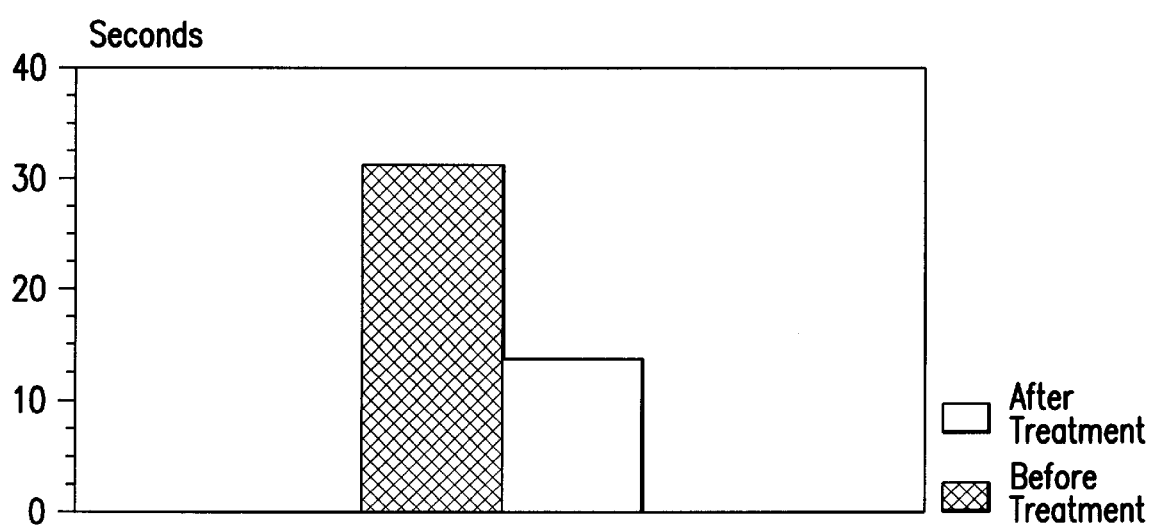
FIG. 25 is a graph showing the effect of bright light therapy and oral atenolol (50 mg daily) on the ability of a patient with Parkinson's disease to walk 6 metres before and after 2 weeks of treatment.

As shown in FIG. 25 the time taken to walk a 3 metre path and return was 31.3 seconds before treatment to 13.5 seconds after treatment. Similarly, the time taken to lift her foot to her knee and return it to the floor 10 times went from 58 s(R) 65 s(L) before treatment to 44 seconds for either leg two weeks after treatment. Similarly, on other motor tests the patient showed improvement after treatment and the memory loss and her mental state improved, permitting her to decrease her daily dose of 1-dopa. Her tremor and rigidity also improved. The patient also presented as thin with a poor appetite and unable to gain weight during the course of her disease but gained 3 kilos in body weight after 2 weeks of treatment. Her increased movement permitted her to increase her daily activities and her quality of life greatly improved.

Figure 26:
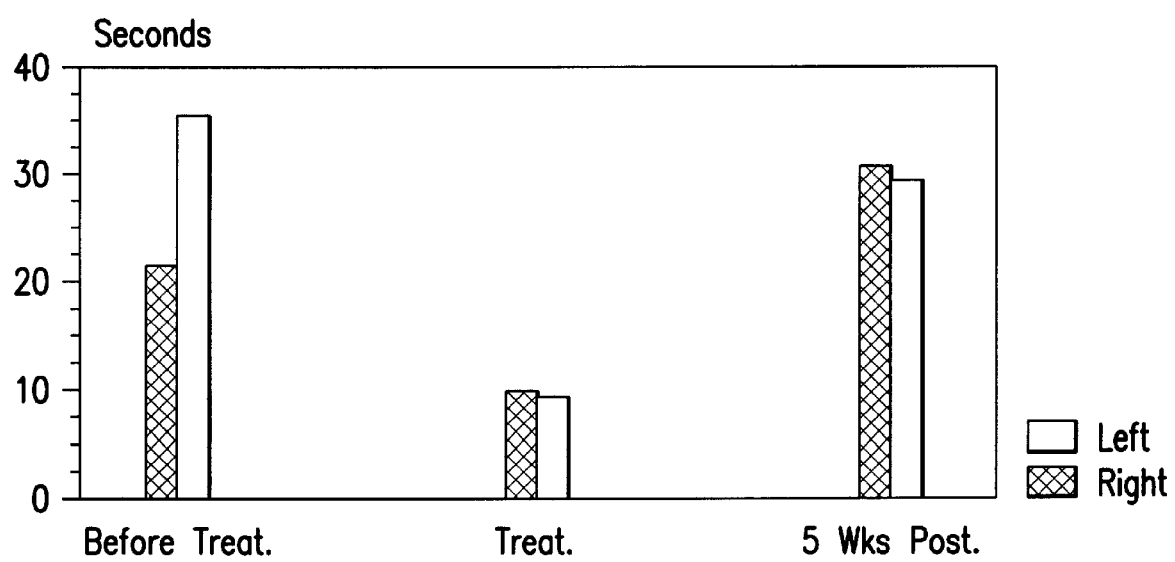
FIG. 26 is a graph showing the effect of bright light therapy and oral atenolol (50 mg daily) on the ability of a patient with Parkinson's disease to touch their toe to their inner knee (x 10). Measurements were taken before treatments commencing after 2 weeks of treatments and 5 weeks after treatments were discontinued.

A second patient, diagnosed with Parkinson's disease at least 10 years previously was tested on the same tests as the first patient. The effect that bright light therapy (1000 lux) 1 hour in the morning and 1 hour at night with Atenolol 50 mg before retiring had on the ability to perform leg movements is shown in FIG. 26.

The latency required to touch her knee with her foot and return to the floor 10 times improved dramatically after 5 weeks of treatment. When the patient was taken off the treatment for 5 weeks her performance deteriorated.

EXAMPLE 7

The compound ML-23, was tested in the 6-OHDA model described in EXAMPLE 1 using a 12 hr light/12 hr dark cycle. Briefly, animals were subject to 13 days controlled observation, on day 14 they were injected with 6-OHDA. Animals in the treatment group were given melatonin antagonist (ML-23 in DMSO (3 mg per mL)) therapy (3 mg/kg/ml, interperitoneal injection (ip)) once on the day of 6-OHDA injection and then twice daily for the 3 subsequent days.

ML-23 prevented the development of severe motor impairment typically exhibited by 6-OHDA treated rats. ML-23 prevented the severe body weight loss characteristically seen in 6-OHDA treated animals. While 3 out of 7 animals in the 6-ODHA/vehicle group died within 6 days after treatment, all rats treated with ML-23 recovered and were capable of regulating their body weight. Horizontal and vertical movement, particularly at night, were significantly improved by the regimen of ML-23 employed. The latency to perform the 3 motor tests (latency to retract a limb, latency to step, and latency to ambulate) were also improved during the test and recovery periods after treatment with ML-23. In summary, all animals injected with ML-23 following 6-ODHA injection performed better than those treated with vehicle following 6-ODHA injection.

EXAMPLE 8

A second melatonin antagonist, S-20928, was tested in the 6-OHDA model described in EXAMPLES 1 and 7. At a dose of 1 mg/kg ip, S-20928 is capable of repairing the most resilient consequence of DA degeneration in any pre-clinical model of PD; that is, body weight (30, 31). Furthermore, in doing so, S-20928 decreases the morbidity of the disease and increases survival time.

REFERENCES

1. Chuang, J. I. and Ling, M. T. 1. Pineal Res., 17, 11, 1994.
2. Bradbury, A. J. et al. In: The Pineal Gland Endocrine Aspects., 327, 1985.
3. Cotzias, G. C., etal. Science, 173, 450,1971.
4. Burton, S. et al. Experientia, 47, 466, 1991.
5. Anton-Tay, F. Proc. 4th Int. Cong. Endo., v 273, 18, 1972.
6. Mclsaac, W. M. et al. Post Grad. Med., 30, 111, 1961.
7. Miles, A. and Philbrick, D. R. S. Biol. Psychiatry, 23, 405, 1988.
8. Femer, I. N. etal. Clin. Endocrinology, 17, 181, 1982. Fanget, F. et al. Biol. Psychiatry, 25, 499, 1989.
9. Hoen, M. M. el al. J. Neurol. Neurosurg. & Psychiatry, 39, 941, 1976.
10. Sandyk, R & Kay, S. R., Int. J. Neurosci., 55, 1, 1990.
11. Horobin, D. Lancet Vol 1, p. 529, 1979.
12. Altschule, M. D. New Eng. J. Med., 257, 919, 1957. Kitay, J. I. & Altschule, M. D. In: The Pineal Gland: A Review of the Physiologic Literature, p.280, 1954.
13. Eldied, S. H. New. Eng. J. Med., 263, 1330, 1960.
14. Hanssen, T. et al. Arch Gen. Psychiatry, 37, 685, 1980.
15. Smith, J. A. el al, J. Pharm. Pharmacol. (Comm.) 31, 246, 1979.
16. Smith, J. A. et at, J, Pharm, Phaumacol. (Coinmm.) 31, 246, 1979.
17. Smith, J.A. et al, Clin. Endocrin. 14, 75, 1981.
18. Anton-Tay, F. Proc. 4th Int. Cong. Endo v 273, p. 18, 1972.
19. Cotzias, G. C. Ann. Rev. Med. 22, 305, 1971.
20. Papavasiliou, P. S., J.A.M.A 221, 88, 1972.
21. Sandyk, P. Int. J. Neurosci. 50, 83, 1990. Sandyk, R. Int. J. Neurosci. 51, 73, 1990.
22. Anton-Tay, F. Proc. 4th Int. Cong. Endo. v 273, p. 18, 1972.
23. Papavasiliou, P. S., J.A.M.A. 221, 88, 1972.
24. Vaughan, G. M. et al, In: Pineal Function, p.19, 1981.
25. Hardeland, R. et al, Neurosci. Biobehav. Rev., 17, 347, 1993.
26. Jenner, P. et al, In: The Assessment and Therapy of Parkinsonism, p.17, 1990.
27. Kennedy, S. H. et al, Arch Gen Psych. 46, 73, 1989.
28. Mortola, J. F. el al, J. Clin. Endocrin. Metab. 77, 1540, 1993.
29. Ferrari, E. et al, Biol. Psychiatry, 27, 1007, 1990.
30. Stein, L. & Wise, C. D., Science, 171, 1032, 1971.
31. Dunnett, S. B., et al, Trends Neurosci, 6, p.266–70 (1983)
32. Dunnet, S. B., and Björklund, A., Appetite, 5, p.263–65 (1984)

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

What is claimed is:

1. A method for the treatment and/or prophylaxis of a neurological or neuropsychiatric disorder associated with altered dopamine function which comprises administering to a patient in need of such treatment or prophylaxis an effective amount of a compound of formula (1)

$$
\text{(1)}
$$

[Structure: indole with CH$_3$O substituent and CH$_2$CH$_2$NH linker to a phenyl ring bearing X and NO$_2$; indole 2-position bears Y]

where X is —NO$_2$ or —N$_3$ and Y is H or I.

2. A method according to claim 1, wherein X is —NO$_2$ and Y is H.

3. A method according to claim 1, wherein said neurological or neuropsychiatric disorder is selected from the group consisting of movement disorders and psychiatric disorders characterized by anxiety.

4. A method according to claim 3, wherein said neurological or neuropsychiatric disorder is selected from the group consisting of Huntingdon's chorea, periodic limb movement syndrome, restless leg syndrome (akathesia), Tourrette's syndrome, Sundowner's syndrome, schizophrenia, Pick's disease, Punch drunk syndrome, progressive subnuclear palsy, Korsakow's (Korsakoff's) syndrome, multiple sclerosis, Parkinson's disease, malignant syndrome, acute dystonia, stroke, trans-ischemic attack, tardive dyskinesia and multiple systems atrophy (Parkinson's plus).

5. A method according to claim 3, wherein the movement disorder is selected from Parkinson's disease, schizophrenia, restless leg syndrome and tardive diskinesia.

6. A method according to claim 5, wherein the movement disorder is Parkinson's disease.

7. A method according to claim 3, wherein said neurological or neuropsychiatric disorder is selected from the group consisting of panic disorder, agoraphobia, obsessive-compulsive disorder, post traumatic stress disorder, acute stress disorder, generalized anxiety disorder, and anxiety disorders due to depression.

8. A method according to claim 7, wherein said neurological or neuropsychiatric disorder is generalized anxiety disorder.

9. A method according to claim 1, wherein said neurological or neuropsychiatric disorder is anorexia cachexia or anorexia nervosa.

10. A method according to claim 1, wherein said neurological or neuropsychiatric disorder is Alzheimer's disease or dementia.

11. A method according to claim 1 or 2, wherein said compound is administered in combination with light therapy.

12. A method according to claim 1 or 2, wherein said compound is administered in combination with surgical ablation or destruction of the pineal gland.

13. A method according to claim 1 or 2, wherein said compound is administered in combination with a drug which alters dopamine function.

14. A method according to claim 1 or 2, wherein said compound is administered in combination with a β-adrenergic antagonist, a calcium channel blocker or a melanocyte stimulating hormone.

15. A method according to claim 13, wherein said drug therapy which alters dopamine function comprises the administration of a dopamine receptor blocker or a β-adrenergic receptor antagonist.

16. A method according to claim 1 or 2, wherein said compound is administered within the range of 0.01 to 50 mg per kg body weight per day.

17. A method according to claim 16, wherein said compound is administered within the range of 0.5 to 10 mg per kg body weight per day.

18. A method according to claim 16, wherein said compound is administered as 2 to 6 sub-dose administrations throughout the day or in the form of a controlled release of the compound.

19. A method according to claim 1 or 2, wherein said compound is administered orally, by implant, rectally, by inhalation, by insufflation, topically, vaginally or parenterally.

20. A method according to claim 1 or 2, wherein said compound is administered in a composition further comprising one or more pharmaceutically acceptable carriers, diluents, adjuvants or excipients.

* * * * *

UNITED STATES PATENT AND TRADEMARK OFFICE
CERTIFICATE OF CORRECTION

PATENT NO.    : 6,310,085 B1
DATED         : October 30, 2001
INVENTOR(S)   : Gregory Lynn Willis It is certified that error appears in the above-identified patent and that said Letters Patent is hereby corrected as shown below:

Title page,
Item [63], Related U.S. Application Data, the following information should be inserted:
-- [30]  Foreign Application Priority Data
   October 4, 1996 (AU) ............PO2745/96 --

Signed and Sealed this

Twenty-fifth Day of February, 2003

JAMES E. ROGAN
*Director of the United States Patent and Trademark Office*

UNITED STATES PATENT AND TRADEMARK OFFICE
CERTIFICATE OF CORRECTION

PATENT NO.   : 6,310,085 B1
DATED        : October 30, 2001
INVENTOR(S)  : Gregory Lynn Willis It is certified that error appears in the above-identified patent and that said Letters Patent is hereby corrected as shown below:

<u>Column 18,</u>
Lines 32-42, Formula (1) should read as follows:

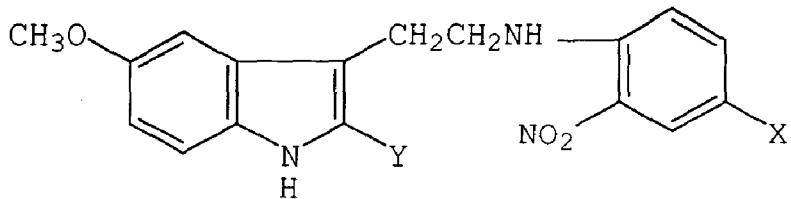

Signed and Sealed this

Ninth Day of September, 2003

JAMES E. ROGAN
*Director of the United States Patent and Trademark Office*